(12) United States Patent
Porter

(10) Patent No.: US 11,730,498 B2
(45) Date of Patent: Aug. 22, 2023

(54) MECHANICALLY RESONANT PULSE RELIEF VALVE AND METHODS OF USE FOR ASSISTED CLEARING OF PLUGGED ASPIRATION

(71) Applicants: STRYKER CORPORATION, Kalamazoo, MI (US); STRYKER EUROPEAN OPERATIONS LIMITED, Carrigtwohill (IE)

(72) Inventor: Stephen Porter, Piedmont, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 337 days.

(21) Appl. No.: 17/133,684

(22) Filed: Dec. 24, 2020

(65) Prior Publication Data

US 2021/0228222 A1 Jul. 29, 2021

Related U.S. Application Data

(60) Provisional application No. 62/965,115, filed on Jan. 23, 2020.

(51) Int. Cl.
*A61B 17/22* (2006.01)
*A61M 1/00* (2006.01)

(52) U.S. Cl.
CPC .... *A61B 17/22* (2013.01); *A61B 2017/22079* (2013.01); *A61M 1/804* (2021.05); *A61M 1/81* (2021.05)

(58) Field of Classification Search
CPC ......... A61B 17/22; A61B 2017/22079; A61M 1/804; A61M 1/81; A61M 1/74; A61M 1/75
See application file for complete search history.

(56) References Cited

U.S. PATENT DOCUMENTS 3,565,076 A 2/1971 Kadan
3,659,605 A 5/1972 Sielaff
(Continued)

FOREIGN PATENT DOCUMENTS

WO 2014151209 9/2014
WO WO 2014/151209 9/2014
(Continued)

OTHER PUBLICATIONS

PCT International Search Report and Written Opinion for International Patent Appln. No. PCT/US2020/066993, applicant Stryker Corporation, dated Apr. 14, 2021 (32 pages).

(Continued)

*Primary Examiner* — Julian W Woo
(74) *Attorney, Agent, or Firm* — Vista IP Law Group, LLP

(57) ABSTRACT

An aspiration system comprises an aspiration catheter, an aspiration source fluidly coupled to the aspiration catheter to create an aspiration flow path between the aspiration catheter and the aspiration source, a pressurized fluid source, and a passive pressure oscillation assembly fluidly coupled between the pressurized fluid source and the aspiration flow path. The passive pressure oscillation assembly is configured for being operated between a normal mode that prevents fluid communication between the pressurized fluid source and the aspiration flow path, and an oscillatory mode that pulses fluid communication between the pressurized fluid source and the aspiration flow path. The passive pressure oscillation assembly is configured for being triggered to switch from the normal mode to the oscillatory mode in response to a clog in the aspiration catheter.

21 Claims, 10 Drawing Sheets

(56) References Cited

U.S. PATENT DOCUMENTS

| | | | |
|---|---|---|---|
| 3,955,574 | A | 5/1976 | Rubinstein |
| 4,447,226 | A | 5/1984 | Mayoral |
| 6,228,056 | B1 | 5/2001 | Boehringer et al. |
| 10,531,883 | B1 * | 1/2020 | Deville .................. A61M 1/75 |
| 2016/0058614 | A1 | 5/2016 | Ross et al. |
| 2017/0143880 | A1 | 5/2017 | Luxon et al. |

FOREIGN PATENT DOCUMENTS

| | | |
|---|---|---|
| WO | 2019115809 | 6/2019 |
| WO | WO 2021/150348 | 7/2021 |

OTHER PUBLICATIONS

International Search Report and Written Opinion for International Appln. No. PCT/US2022/038643, Applicant Stryker Corporation, dated Nov. 16, 2022 (14 pages).

\* cited by examiner

MECHANICALLY RESONANT PULSE RELIEF VALVE AND METHODS OF USE FOR ASSISTED CLEARING OF PLUGGED ASPIRATION

RELATED APPLICATION DATA

The present application claims the benefit of priority under 35 U.S.C. § 119 to U.S. provisional patent application Ser. No. 62/965,115, filed Jan. 23, 2020.

FIELD OF THE INVENTION

The present disclosure relates generally to medical devices and intravascular medical procedures and, more particularly, to devices and methods for aspirating objects from the anatomy, e.g., a clot from the vasculature of the patient.

BACKGROUND OF THE INVENTION

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One cause of insufficient or irregular blood flow is a blockage within a blood vessel referred to as a blood clot or thrombus. Blood clots or thrombi may embolize and form an embolus in a patient vasculature. Thrombi can occur for many reasons, including damage to the arterial wall from atherosclerotic disease, trauma caused by surgery, or due to other causes.

When a thrombus forms, it may effectively stop the flow of blood through the zone of formation. Sometimes such thrombi are harmlessly dissolved in the blood stream. At other times, however, such thrombi may lodge in a blood vessel where they can partially or completely occlude the flow of blood. If the partially or completely occluded vessel feeds blood to sensitive tissue such as, the brain, lungs or heart, for example, serious tissue damage may result. For example, thrombosis of one of the carotid arteries can lead to stroke, because of insufficient oxygen supply to vital nerve centers in the cranium. As another example, if one of the coronary arteries is 100% thrombosed, the flow of blood is stopped in that artery, resulting in a shortage of oxygen carrying red blood cells, e.g., to supply the muscle (myocardium) of the heart wall. Oxygen deficiency reduces or prohibits muscular activity, can cause chest pain (angina pectoris), and can lead to death of myocardium, which permanently disables the heart to some extent. If the myocardial cell death is extensive, the heart will be unable to pump sufficient blood to supply the body's life sustaining needs. Indeed, a large percentage of the more than 1.2 million heart attacks in the United States are caused by blood clots (thrombi) which form within a coronary artery.

When symptoms of an occlusion are apparent, such as an occlusion resulting in a stroke, immediate action should be taken to reduce or eliminate resultant tissue damage. Indeed, clinical data indicates that clot removal may be beneficial or even necessary to improve outcomes. For example, in the peripheral vasculature, clot removal can reduce the need for an amputation by 80 percent. The ultimate goal of any modality to treat these conditions of the arterial or venous system is to remove the blockage or restore patency, quickly, safely, and cost effectively. One approach is to treat a patient with clot dissolving drugs. These drugs, however, do not immediately dissolve the clot from the patient, and are typically ineffective after a predefined window, usually at 2-3 hours after the symptoms arise from the clot. Other approaches involve thrombectomy, i.e., the removal of the clot by aspiration, mechanical retrieval, or a combination thereof. Mechanical retrieval usually involves a deployable mesh-like grid, such as a stent retriever, and is often complicated and dangerous to perform.

Aspiration thrombectomy is generally an effective and common treatment for removing a clot from a blood vessel, especially in the case of ischemic stroke. In a typical endovascular aspiration thrombectomy procedure, a catheter is introduced into the vasculature of the patient until the distal end of a catheter is just proximal to the clot, and a vacuum is applied at the proximal end of the catheter, resulting in the ingestion and subsequent removal of at least a portion of the clot into the catheter. Most aspiration systems are susceptible to tip clogging when the clot that is being aspirated is too large for the aspiration conduit at the distal end of the catheter. Current technology for endovascular thrombectomy in ischemic stroke utilizes static loading. Once tip clogging occurs, the pressure in the system precipitously drops to a level that often results in boiling or cavitation of the aspirate within the system. As a result, water vapor is introduced into the system, thereby decreasing the efficiency of the aspiration, and in turn, making it more difficult, if not impossible, to ingest the clot into the catheter.

In some cases, the clog can be disrupted or forced to squeeze through the aspiration conduit by dynamically or cyclically loading the aspiration conduit, which involves using pressure pulsing to ingest the clogged clot. One method of cyclically loading the aspiration conduit uses a cyclically activated valve or similar configuration to achieve the pressure pulsing by blocking main stream flow. Typically, this is done by hand, or via an electro-mechanical or pneumatic valve which blocks aspirate flow to the pump for a specified time interval. In some instances, pressure sensing feedback has been suggested as a means for determining when to activate the valve. One cyclical loading method, described in Simon S, Grey C P, Massenzo T, et al., "Exploring the efficacy of cyclic vs static aspiration in a cerebral thrombectomy model: an initial proof of concept study," Journal of NeuroInterventional Surgery 2014; 6:677-683 and PCT Publication WO2014151209A8, employs a venting mechanism that is automatically placed in an oscillatory pulse mode in response to the application of vacuum to the aspiration conduit. However, these methods either require user intervention to cyclically load the aspiration conduit in response to the realization that the aspiration conduit it has been clogged, which would distract the user from performing the aspiration procedure at hand, or cyclically load the aspiration conduit immediately upon the application of vacuum to the aspiration conduit, and thus, decreases the efficiency of the aspiration procedure during free flow (i.e., when the aspiration conduit is not clogged).

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. Further, an aspect or an advantage described in conjunction with a particular embodiment of the disclosed inventions is not necessarily limited to that embodiment and can be practiced in any other embodiments even if not so illustrated.

In order to better appreciate how the above-recited and other advantages and objects of the disclosed inventions are obtained, a more particular description of the disclosed inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE ILLUSTRATED EMBODIMENTS

Figure 1:
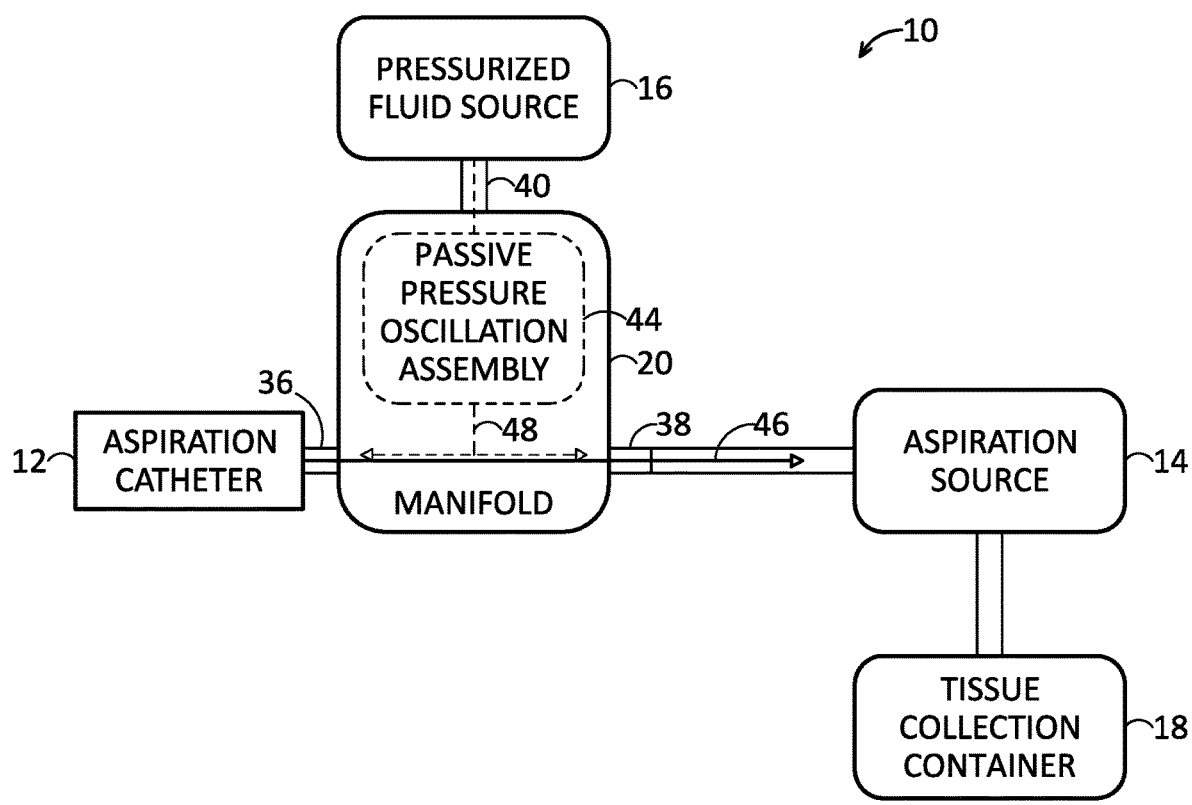
FIG. 1 is a block diagram of one embodiment of an aspiration system constructed in accordance with the present inventions.

Referring to FIG. 1, one embodiment of an occlusion aspiration system 10 constructed accordance with the disclosed inventions will now be described. The occlusion aspiration system 10 generally comprises an aspiration catheter 12, an aspiration source 14, a pressurized fluid source 16, a tissue collection container 18, and a manifold 20.

Figure 2:
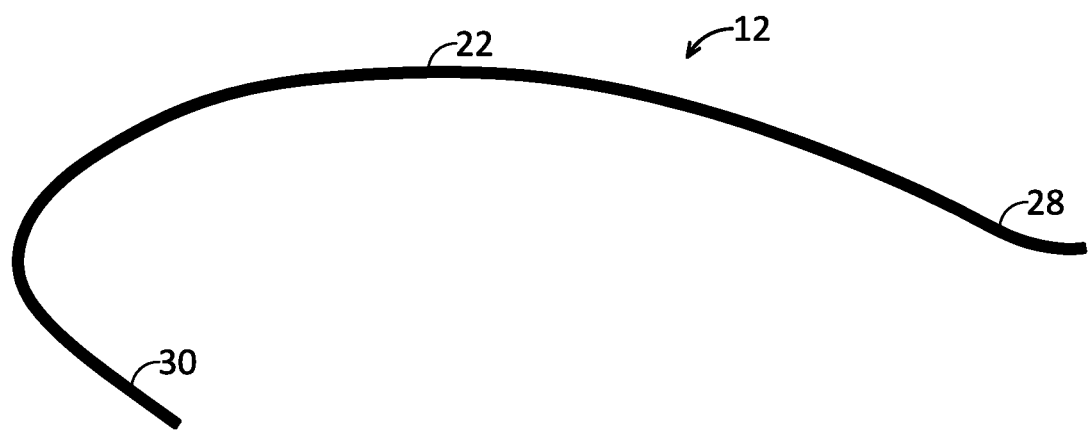
FIG. 2 is a plan view of an exemplary aspiration catheter used in the aspiration system of FIG. 1.
Figure 3:
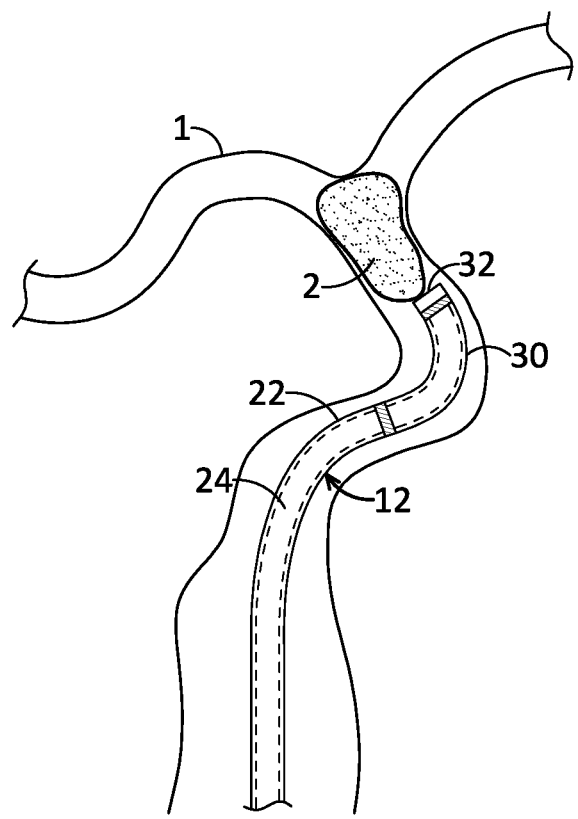
FIG. 3 is a plan view of the distal end of the aspiration catheter of FIG. 2 in use for aspirating an occlusion from the vasculature of a patient.

Referring further to FIGS. 2 and 3, the aspiration catheter 12 comprises an elongated catheter body 22, an aspiration conduit 24 (shown in phantom in FIG. 3) extending through the catheter body 22 between a proximal end 28 and the distal end 30 of the catheter body 22. The proximal end 28 of the aspiration catheter 12 remains outside of a patient 1 and accessible to the operator when the occlusion aspiration system 10 is in use, while the distal end 30 of the catheter body 22 is sized and dimensioned to reach an occlusion 2 (e.g., a clot) with a remote location of the vasculature 1 of the patient, as best shown in FIG. 3. The aspiration catheter 12 comprises a distal inlet port 32 in communication with the aspiration conduit 24 of the aspiration catheter 12, and into which the occlusion 2 is ingested by the aspiration catheter 12.

The aspiration catheter 12 may include a plurality of regions along its length having different configurations and/or characteristics. For example, a distal portion of the catheter body 22 may have an outer diameter less than the outer diameter of a proximal portion of the catheter body 22 to reduce the profile of the distal portion of the catheter body 22 and facilitate navigation in tortuous vasculature. Furthermore, the distal portion of the catheter body 22 may be more flexible than the proximal portion of the catheter body 22. Generally, the proximal portion of the catheter body 22 may be formed from material that is stiffer than the distal portion of the catheter body 22, so that the proximal portion has sufficient pushability to advance through the vasculature 1 of the patient, while the distal portion may be formed of a more flexible material so that it may remain flexible and track more easily over a guidewire to access remote locations in tortuous regions of the vasculature 1. The catheter body 22 may be composed of suitable polymeric materials, metals and/or alloys, such as polyethylene, stainless steel or other suitable biocompatible materials or combinations thereof. In some instances, the proximal portion of the catheter body 22 may include a reinforcement layer, such a braided layer or coiled layer to enhance the pushability of the catheter body 22. The catheter body 22 may include a transition region between the proximal portion and the distal portion of the catheter body 22.

Referring back to FIG. 1, the aspiration source 14 can be, e.g., conventional a pump (e.g., a rotary vane, diaphragm, peristaltic or Venturi pump) or a syringe, configured for generating a low pressure within the aspiration conduit 26 of the aspiration catheter 12. The low pressure is below the ambient air pressure, and thus, can be considered a vacuum capable of aspirating the occlusion 2 within the aspiration conduit 26 of the aspiration catheter 12. The occlusion 2 may be wholly ingested into the aspiration catheter 12 or may be broken up into pieces and ingested piece-by-piece into the aspiration catheter 12. In operation, the aspiration source 14 provides a base level of vacuum for the aspiration catheter 12. This vacuum level may be controlled and adjusted as needed by the user for aspirating tissue. Over any given time period during a tissue removal procedure, the user may set the level of vacuum to be constant or may vary the vacuum level.

The pressurized fluid source 16 may be, e.g., a reservoir containing a liquid, such as saline (e.g., a saline drip bag), or ambient air. It should be appreciated that the fluid source 16 is pressurized to the extent that the fluid has a pressure that is higher than the lowest vacuum level achieved in the aspiration conduit 24 of the aspiration catheter 12 when the aspiration source 14 is operating. Thus, even though the fluid source 16 in the illustrated embodiment may be under low pressure (i.e., at ambient or one atmosphere absolute pressure), the fluid source 16 is pressurized relative to the pressures experienced by the aspiration conduit 24 of the aspiration catheter 12 during operation of the aspiration source 14. The tissue collection container 18 may be any suitable receptacle in fluid communication with the aspiration source 14 via an exhaust line for enabling collection and disposal of aspirated tissue in a sterile manner. Alternatively, the tissue collection container 18 may be located between the aspiration source 14 and the aspiration catheter 12.

The aspiration catheter 12, aspiration source 14, pressurized fluid source 16, and tissue collection container 18 may be conventional in nature.

In contrast, the manifold 20 is unconventional, and provides an interface between the aspiration catheter 12, aspiration source 14, and pressurized fluid source 16 in a manner that facilitates ingestion of the thrombus 2 by the aspiration catheter 12 during no-flow or low-flow conditions (e.g., if the thrombus 2 clogs the aspiration conduit 24 of the aspiration catheter 12 or otherwise there is a flow anomaly in the aspiration circuit of the system 10), while maximizing efficiency of the aspiration process during free-flow conditions (e.g., when the aspiration conduit 24 is not clogged and the aspiration circuit of the system 10 is operating as intended).

The manifold 20 comprise an aspiration inlet 36 coupled to the aspiration catheter 12, and an aspiration outlet 38 coupled to the aspiration source 14, such that an aspiration flow path 46 is formed from the aspiration catheter 12 to the aspiration source 14, and a relief inlet 40 coupled to the pressurized fluid source 16. The manifold 20 may be coupled to the aspiration catheter 12, aspiration source 14, and pressurized fluid source 16 via the use of conventional catheters (not shown) or may alternatively be integrated with the aspiration catheter 12, aspiration source 14, and pressurized fluid source 16 without the use of connectors. The manifold 20 further comprises a passive pressure oscillation assembly 44 coupled between the relief inlet 40 and the aspiration flow path 46. Significantly, the passive pressure oscillation assembly 44 is configured for dynamically loading (i.e., rapidly changing the vacuum level) the aspiration conduit 24 of the aspiration catheter 12, and in particular, cyclically loading the aspiration conduit 24 only during the no-flow or low-flow conditions. The passive pressure oscillation assembly 44 accomplishes this without user input and without the use of electronic sensors. Furthermore, the passive pressure oscillation assembly 44 may be made to be very compact, such that it can be fitted within manifold 20 will little additional bulk. The passive pressure oscillation assembly 44 may be disabled simply be blocking the relief inlet 40.

To this end, the passive pressure oscillation assembly 44 is configured for being operated between a normal mode that prevents fluid communication along a relief path 48 between the pressurized fluid source 16 and the aspiration flow path 46, such that the absolute pressure in the aspiration flow path 46 remains relatively constant and is only acted upon by the aspiration source 14, and an oscillatory mode that pulses fluid communication along the relief path 48 between the pressurized fluid source 16 and the aspiration flow path 46, such that the absolute pressure in the aspiration flow path 46 oscillates within a range of predetermined frequencies. The passive pressure oscillation assembly 44 is configured for being triggered to switch from the normal mode to the oscillatory mode in response to a clog in the aspiration conduit 24 of the aspiration catheter 12 or otherwise a flow anomaly in the aspiration conduit of the system 10, and conversely, for being triggered to switch from the oscillatory mode to the normal mode in response to removal or clearance of the clog from the aspiration conduit 24 of the aspiration catheter 12 or otherwise resolution of the flow anomaly in the aspiration circuit of the system 10. In the illustrated embodiment, fluid communication pulsing between the pressurized fluid source 16 and the aspiration flow path 46 causes pressure pulses to propagate down the aspiration conduit 24 of the aspiration catheter 12 at the predetermined frequency. Simultaneously, fluid communication pulsing between the pressurized fluid source 16 and the aspiration flow path 46 causes fluid backflows to propagate down the aspiration conduit 24 of the aspiration catheter 12.

The passive pressure oscillation assembly 44 may be designed to pulse fluid communication along the relief path 48 between the pressurized fluid source 16 and the aspiration flow path 46 at a predetermined frequency, such that the absolute pressure in the aspiration flow path 46 oscillates at that predetermined frequency. As one example, the predetermined frequency of the pressure oscillations induced in the aspiration flow path 46 by the passive pressure oscillation assembly 44 may match the natural resonance of the fluid column within the aspiration conduit 24 of the aspiration catheter 12, such that energy transfer from the aspiration flow path 46 to the aspiration conduit 24 of the aspiration catheter 12, and thus propagation of the pressure pulses down the aspiration conduit 24 of the aspiration catheter 12, is maximized. As another example, the predetermined frequency of the pressure oscillations induced in the aspiration flow path 46 by the passive pressure oscillation assembly 44 may be selected based on the visco-elastic properties of thrombus 2 expected to be ingested by the aspiration catheter 12. That is, a clogged thrombus 2 with a softer consistency may be more susceptible to maceration, and thus subsequent ingestion, in response to relatively low-frequency, high-amplitude oscillations, whereas a clogged thrombus 2 with a harder consistency may be more susceptible to maceration, and thus subsequent ingestion, in response to relatively high-frequency, low-amplitude oscillations.

The oscillation of the passive pressure oscillation assembly 44 may optionally cause sound to emanate, and can serve as an automatic audible signal to the user that a clog in the aspiration conduit 24 of the aspiration catheter 12 has occurred. In an optional embodiment, the passive pressure oscillation assembly 44 may be designed to pulse fluid communication between the pressurized fluid source 16 and the aspiration flow path 46 simultaneously at two or more different frequencies. For example, because determining the type of material properties of the thrombus 2 will not be known ahead of time, it may be desirable to pulse fluid communication between the pressurized fluid source 16 and the aspiration flow path 46 simultaneously at a relatively high frequency and at a relatively low frequency, such that the pressure profile in the aspiration conduit 24 of the aspiration catheter 12 is a composite of the low-frequency and high-frequency oscillations.

In the illustrated embodiment, the passive pressure oscillation assembly 44 takes advantage of the correlation between the different flow conditions of the aspiration catheter 12 and the resulting fluid pressure levels in the aspiration flow path 46. In particular, it is expected that, in the case of a no-flow or low-flow condition where there is a clog in the aspiration conduit 24 of the aspiration catheter 12, or otherwise a flow anomaly in the aspiration circuit of the system 10, the vacuum in the aspiration flow path 46 will precipitously increase (i.e., the absolute pressure in the aspiration flow path 46 will precipitously decrease), thereby causing the negative pressure differential between the external ambient pressure and the aspiration flow path 46 to increase to a very high level (e.g., at least −55 kPa), which, assuming no intervention by the passive pressure oscillation assembly 44, may even cause boiling or cavitation of the aspirate within the aspiration flow path 46 (e.g., if the such negative pressure differential below −95 kPa). In contrast, it is also expected that, in the case of a free-flow condition where the aspiration catheter 12 has been unclogged, or otherwise, the flow anomaly in the aspiration circuit of the system 10 has been resolved, the vacuum in the aspiration flow path 46 will precipitously decrease (i.e., the absolute pressure in the aspiration flow path 46 will precipitously increase) to a lower level (e.g., less than −50 kPa), thereby causing the negative pressure differential between the external ambient pressure and the aspiration flow path 46 to decrease to a lower level. The passive pressure oscillation assembly 44 keys off these negative pressure differentials when switching between the normal mode and the oscillatory mode.

To this end, the passive pressure oscillation assembly 44 comprises an inlet port 50 (shown in FIG. 5) in fluid communication with the pressurized fluid source 16 and an outlet port 52 (shown in FIG. 5) in fluid communication with the aspiration flow path 46, such that the passive pressure oscillation assembly 44 is exposed to a negative pressure differential between pressurized fluid source 16 and the fluid in the aspiration flow path 46. The passive pressure oscillation assembly 44 is triggered to switch from the normal mode and the oscillatory mode, and conversely, from the oscillatory mode to the normal mode, based on this negative pressure differential.

In particular, the passive pressure oscillation assembly 44 is designed to be triggered to switch from the normal mode to the oscillatory mode in response to a drop in absolute pressure in the aspiration flow path 46 that creates a negative activation pressure differential between the inlet port 50 and the outlet port 52 of the passive pressure oscillation assembly 44 correlated to the negative pressure differential between the aspiration flow path 46 and the blood pressure experienced by the aspiration catheter 12 when the aspiration conduit 24 of the aspiration catheter 12 is clogged or the aspiration circuit of the system 10 otherwise experiences a flow anomaly (no-flow or low-flow condition); and conversely, the passive pressure oscillation assembly 44 is designed to be triggered to switch from the oscillatory mode to the normal mode in response to an increase in absolute pressure in the aspiration flow path 46 that creates a negative cessation pressure differential between the inlet port 50 and the outlet port 52 of the passive pressure oscillation assembly 44 correlated to the negative pressure differential between the aspiration flow path 46 and the blood pressure experienced by the aspiration catheter 12 when the aspiration conduit 24 of the aspiration catheter 12 is unclogged or the aspiration circuit of the system 10 is operating as intended (free-flow condition).

In the case where the pressurized fluid source 16 is at the external ambient pressure, the negative activation pressure differential of the passive pressure oscillation assembly 44 will essentially differ from the negative pressure differential between the aspiration flow path 46 and the blood pressure experienced by the aspiration catheter 12 by a known offset during a no-flow or low-flow condition, and likewise, the negative cessation pressure differential of the passive pressure oscillation assembly 44 will essentially differ from the negative pressure differential between the aspiration flow path 46 and the blood pressure experienced by the aspiration catheter 12 by a known offset during a free-flow condition. In this manner, the passive pressure oscillation assembly 44 may be configured to self-calibrate to a time-varying ambient external environment.

In this case, the range in which the negative activation pressure differential of the passive pressure oscillation assembly 44 is designed may have an upper limit of −55 kPa, such that the passive pressure oscillation assembly 44 is quickly triggered to switch from the normal mode to the oscillatory mode, but not so low that the passive pressure oscillation assembly 44 is triggered to switch from the normal mode to the oscillatory mode during active and productive ingestion of the thrombus 2 into the distal end 30 of the aspiration catheter 12, and may have a lower limit of −95 kPa to ensure that the boiling point of fluid (i.e. blood at 37° C.) in the aspiration flow path 46 is never reached, although it should be appreciated that the passive pressure oscillation assembly 44 may be designed to have a negative activation pressure differential that falls anywhere within the range of −55 kPa to −95 kPa. The negative cessation pressure differential of the passive pressure oscillation assembly 44 should be designed relative to the negative activation pressure differential of the passive pressure oscillation assembly 44, preferably, substantially less than the negative activation pressure differential (e.g., within the range of 10 kPa-25 kPa greater than the negative activation pressure differential), such that hysteresis is built into the passive pressure oscillation assembly 44. In this manner, the pressure oscillations induced in the aspiration flow path 46 by the passive pressure oscillation assembly 44 will not inadvertently trigger the passive pressure oscillation assembly 44 back into the normal mode until the aspiration catheter 12 is in a free-flow condition. It should be noted that, in low-resonant frequency scenarios, the negative activation pressure differential and the negative cessation pressure differential may be the same, in which case, the passive pressure oscillation assembly 44 will be re-triggered after each increase in the negative pressure differential in the aspiration flow path 46 to switch from the normal mode to the oscillation mode in response to the decrease in the absolute pressure in the aspiration flow path 46 caused by the aspiration source 18.

In an optional embodiment, the passive pressure oscillation assembly 44 may be designed with multiple negative activation pressure differentials, and correspondingly, multiple negative cessation pressure differentials. For example, the passive pressure oscillation assembly 44 may be designed to have a first negative activation pressure differential, e.g., at −50 kPa, such that the passive pressure oscillation assembly 44 is triggered to switch from the normal mode to a relatively fast oscillatory mode to facilitate ingestion of the thrombus 2 into the distal end 30 of the aspiration catheter 12 prior to a clog in the aspiration conduit 24 of the aspiration catheter 12. Operation of the passive pressure oscillation assembly 44 in the relatively high oscillatory mode may cause high frequency, but low volume, pulses to propagate down the aspiration conduit 24 of the aspiration catheter 12, thereby facilitating ingestion of the thrombus 2 without overly impeding volume flow. The passive pressure oscillation assembly 44 may be further designed to have a second negative activation pressure differential, e.g., at −55 kPa, such that the passive pressure oscillation assembly 44 is triggered to operate in a relatively slow oscillatory mode to facilitate clearing of a thrombus 2 that is clogged in the distal end 30 of the aspiration catheter 12. Operation of the passive pressure oscillation assembly 44 in the relatively high oscillatory mode may cause low frequency, but high volume, pulses to propagate down the aspiration conduit 24 of the aspiration catheter 12 in an attempt to dislodge the clogged thrombus 2 from the distal end 30 of the aspiration catheter 12. Thus, if the thrombus 2 is ingested without ever clogging the distal end 30 of the aspiration catheter 12, only the relatively fast oscillatory mode of the passive pressure oscillation assembly 44 will be triggered, whereas the relatively slow oscillatory mode of the passive pressure oscillation assembly 44 will only be triggered when the thrombus 2 clogs the distal end 30 of the aspiration catheter 12.

It should be appreciated that the pressurized fluid source 16 may have a pressure substantially different from the external ambient pressure experienced by the aspiration catheter 12, in which case, the negative activation pressure differential of the passive pressure oscillation assembly 44 will be substantially different from the negative pressure differential between the aspiration flow path 46 and the ambient external environment experienced by the aspiration catheter 12 during a no-flow or low-flow condition, and likewise, the negative cessation pressure differential of the passive pressure oscillation assembly 44 will be substantially different from the negative pressure differential between the aspiration flow path 46 and the ambient external environment experienced by the aspiration catheter 12 during a free-flow condition. In this latter case, this difference can be taken into account when designing the negative activation pressure differential and negative cessation pressure differential of the passive pressure oscillation assembly 44. For example, if the pressurized fluid source 16 has a pressure substantially higher than the external ambient pressure, then the passive pressure oscillation assembly 44 should be designed to a negative activation pressure differential and negative cessation pressure differential that is higher to account for the higher fluid pressure that will be experienced by the inlet port 50 of the passive pressure oscillation assembly 44.

Figure 4:
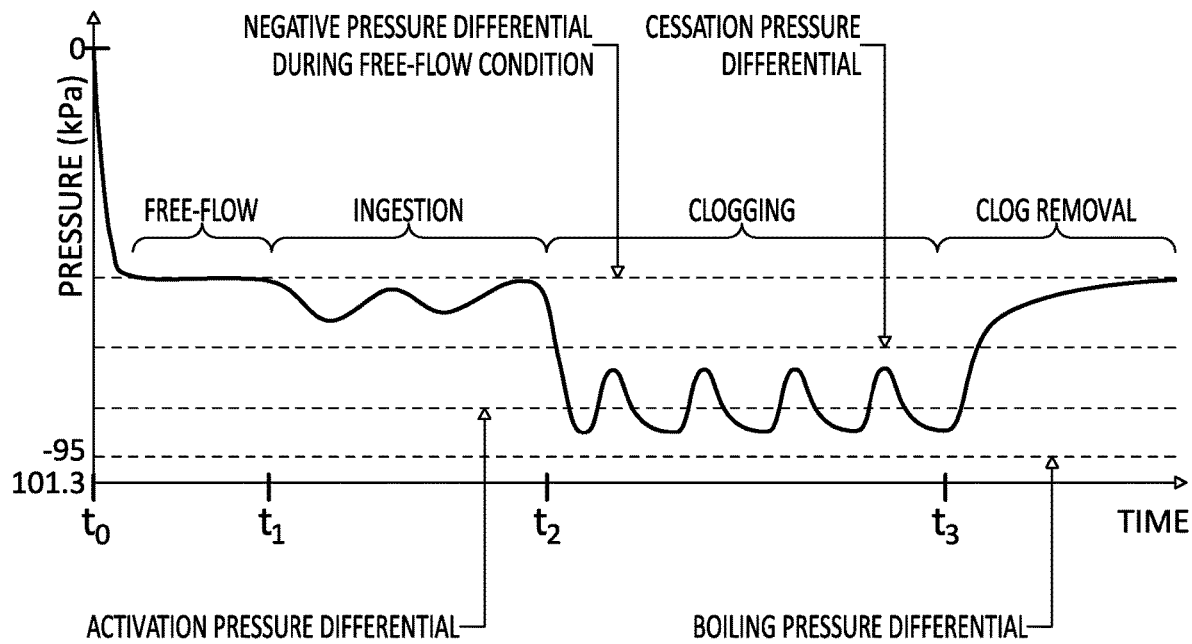
FIG. 4 is a timing diagram illustrating the negative pressure differential between a pressurized fluid source and an aspiration flow path created in the aspiration system of FIG. 1 over time.

As one example, and with reference to FIG. 4, the aspiration source 14 is first activated, such that the aspiration catheter 12 is in a free-flow condition between arbitrary time $t_0$ and $t_1$, and the negative pressure differential between the absolute pressure in the aspiration flow path 46 and the external ambient pressure experienced by the aspiration catheter 12 (in this case, the negative pressure differential between the inlet port 50 and the outlet port 52 of the passive pressure oscillation assembly 44) is at a free-flow negative pressure differential where the aspiration catheter 12 is only ingesting blood. During this time, the passive pressure oscillation assembly 44 remains in the normal mode. In this manner, the aspiration efficiency of the system 10 is maximized during free-flow conditions.

Between arbitrary time $t_1$ and arbitrary time $t_2$, the thrombus 2 is actively being ingested into the distal end 30 of the aspiration catheter 12, such that the negative pressure differential between the absolute pressure in the aspiration flow path 46 and the external ambient pressure experienced by the aspiration catheter 12 drops below the free-flow negative pressure differential, but not below the negative activation pressure differential of the passive pressure oscillation assembly 44, which is designed for a no-flow or low-flow condition indicative of a clogged aspiration catheter 12 or flow anomaly in the aspiration conduit of the system 10. During arbitrary time to and time $t_2$, the passive pressure oscillation assembly 44 remains in the normal mode.

At arbitrary time $t_2$, however, the aspiration catheter 12 becomes clogged with the thrombus 2, resulting in a precipitous decrease in the negative pressure differential between the absolute pressure in the aspiration flow path 46 and the external ambient pressure experienced by the aspiration catheter 12 to a level below the negative activation pressure differential, which in the illustrated case, is at −75 kPa. Thus, at or just after the arbitrary time $t_2$, the clogged aspiration catheter 12 (no-flow or low-flow condition) triggers the passive pressure oscillation assembly 44 to switch from the normal mode to the oscillatory mode, resulting in pressure oscillations in the aspiration flow path 46 that cause pressure pulses to propagate down the aspiration conduit 24 of the aspiration catheter 12, thereby facilitating clearance of the clogged thrombus 2 at the distal end 24 of the aspiration catheter 12 at the arbitrary time $t_3$. Clearance of the clogged thrombus 2 at the distal end 24 of the aspiration catheter 12 results in a precipitous increase in the negative pressure differential between the absolute pressure in the aspiration flow path 46 and the external ambient pressure experienced by the aspiration catheter 12 to a level above the negative cessation pressure differential, which in the illustrated case, is at −50 kPa. Thus, at or just after the arbitrary time $t_3$, the cleared aspiration catheter 12 (free-flow condition) triggers the passive pressure oscillation assembly 44 to switch from the oscillatory mode to the normal mode, ceasing pressure oscillations in the aspiration flow path 46, and thus ceasing pressure pulses from propagating down the aspiration conduit 24 of the aspiration catheter 12.

In the optional embodiment where the passive pressure oscillation assembly 44 operates in multiple oscillatory modes (e.g., a high frequency oscillatory mode and a low frequency oscillatory mode), the passive pressure oscillation assembly 44 may be operated in the high frequency oscillatory mode between the arbitrary time $t_1$ and arbitrary time $t_2$, such that active ingestion of the thrombus 2 into the distal end 30 of the aspiration catheter 12 is facilitated by the high-frequency, but low volume, pressure pulses propagating down the aspiration conduit 24 of the aspiration catheter 12, and then if the thrombus 2 clogs the distal end 30 of the aspiration catheter 12, may be then operated in the low frequency oscillatory mode between the arbitrary time $t_2$ and the arbitrary time $t_3$, such that clearance of the clogged thrombus 2 from the distal end 30 of the aspiration catheter 12 is facilitated by the low-frequency, high volume, pressure pulses propagating down the aspiration conduit 24 of the aspiration catheter 12.

Figure 5:
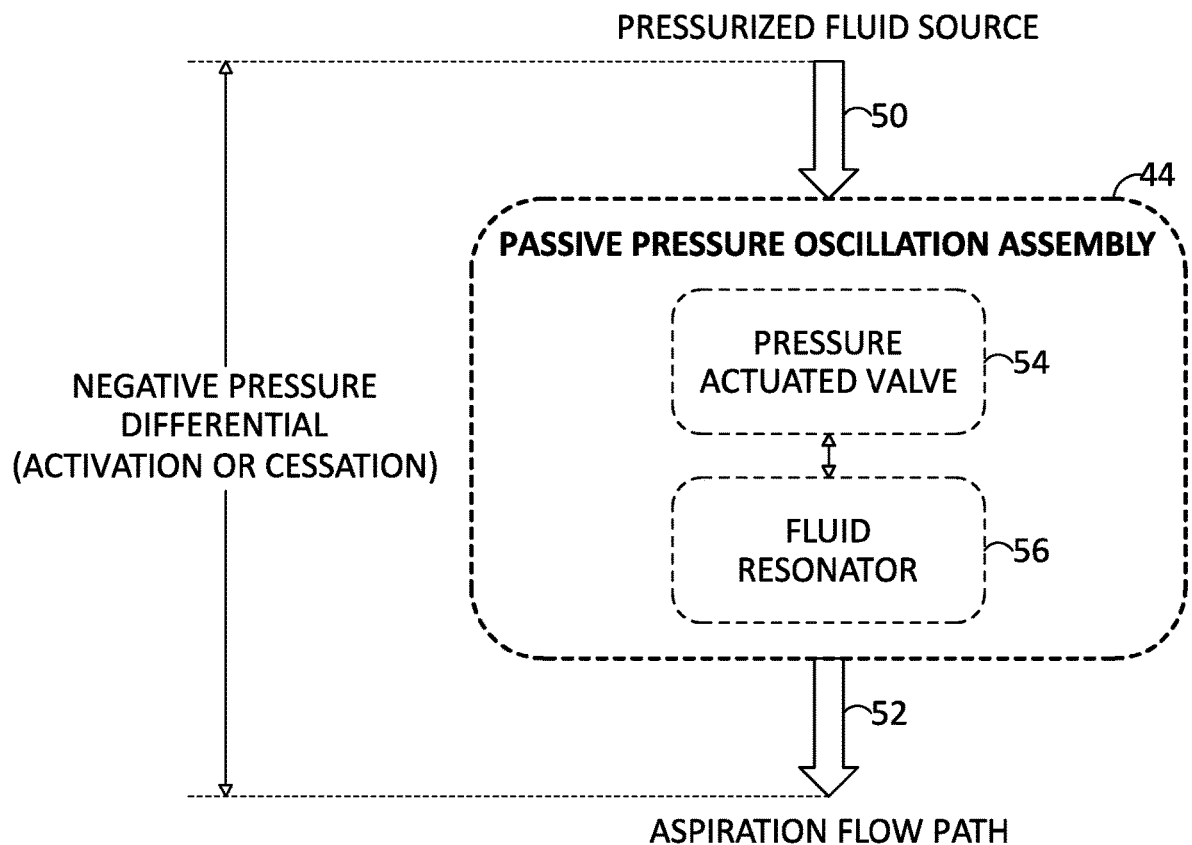
FIG. 5 is a block diagram of one embodiment of a passive pressure oscillation assembly used in the aspiration system of FIG. 1.

Referring to FIG. 5, the passive pressure oscillation assembly 44 comprises a pressure actuated valve 54 and a fluid (e.g., hydraulic or pneumatic) resonator 56. The pressure actuated valve 54 is configured for opening in response to a drop in absolute pressure in the aspiration flow path 28 that creates a negative activation pressure differential between the inlet port 50 and the outlet port 52 (e.g., indicative of a clog in the aspiration conduit 24 of the aspiration catheter 12), thereby allowing the flow of fluid from the pressurized fluid source 16 through the pressure actuated valve 54; and conversely, for closing in response to an increase in absolute pressure in the aspiration flow path 28 that creates a negative cessation pressure differential between the inlet port 50 and the outlet port 52 (e.g., indicative of the removal or clearance of a clog from the aspiration conduit 24 of the aspiration catheter 12), thereby preventing the flow of fluid from the pressurized fluid source 16 through the pressure actuated valve 54. The fluid resonator 56 is configured for resonating at a predetermined frequency in response to the flow of fluid from the pressurized fluid source 16 through the pressure actuated valve 54, thereby pulsing the fluid communication between the pressurized fluid source 16 and the aspiration flow path 46 at the predetermined frequency; and conversely, configured for ceasing resonation in response to the prevention of the flow of fluid from the pressurized fluid source 16 through the pressure actuated valve 54.

In one embodiment, the pressure actuated valve 54 and fluid resonator 56 are mechanically coupled to each other. In this embodiment, although the mechanically coupled pressure actuated valve 54 and fluid resonator 56 must be dependently designed to satisfy both the opening and resonant frequency criteria, it results in a simpler mechanical design that can be more easily implemented into the passive pressure oscillation assembly 44. In another embodiment, the pressure actuated valve 54 and fluid resonator 56 are mechanically decoupled from each other. In this embodiment, the mechanically decoupled pressure actuated valve 54 and fluid resonator 56 allows the opening/closing criteria and resonant frequency criteria to be independently optimized, although resulting in a mechanical design that may be more complicated than the mechanical design of the embodiment with the mechanically coupled pressure actuated valve 54 and fluid resonator 56.

As discussed above, the passive pressure oscillation assembly 44 may optionally be designed to have two negative activation pressure differentials, and/or two negative cessation pressure differentials, and/or pulse fluid communication between the pressurized fluid source 16 and the aspiration flow path 46 simultaneously at two different frequencies.

In an alternative embodiment, the fluid resonator 56 pulses fluid communication between the pressurized fluid source 50 and the aspiration flow path 46 automatically in response to a clog in the aspiration catheter 12 by interrupting the aspiration flow path 46, such that the pulsing fluid communication between the pressurized fluid source 50 and the aspiration flow path 46 is directed towards the aspiration catheter 12.

Figure 6:
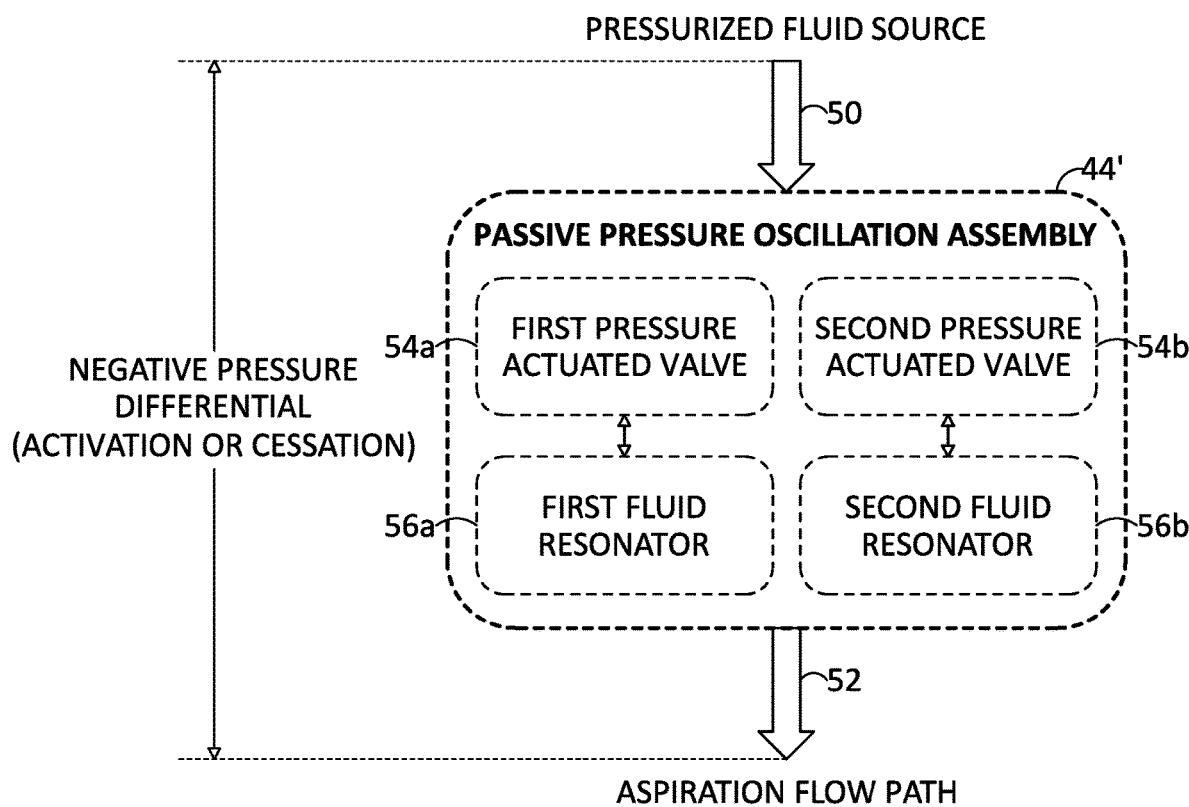
FIG. 6 is a block diagram another embodiment of a passive pressure oscillation assembly used in the aspiration system of FIG. 1.

Referring to FIG. 6, an alternative embodiment of a passive pressure oscillation assembly 44' comprises two parallel sets of pressure actuated valve assemblies and fluid resonators. In particular, the passive pressure oscillation assembly 44' comprises a first pressure actuated valve 54a, a first fluid resonator 56a, a second pressure actuated valve 54b, and a second fluid resonator 56b.

The first pressure actuated valve 54a is configured for opening in response to a drop in absolute pressure in the aspiration flow path 28 that creates a first negative activation pressure differential between the inlet port 50 and the outlet port 52, thereby allowing a flow of fluid from the pressurized fluid source 16 through the first pressure actuated valve 54a; and conversely, for closing in response to an increase in absolute pressure in the aspiration flow path 28 that creates a first negative cessation pressure differential between the inlet port 50 and the outlet port 52, thereby preventing the flow of fluid from the pressurized fluid source 16 through the pressure actuated valve 54. The first fluid resonator 56a is configured for resonating at a first predetermined frequency in response to the flow of fluid from the pressurized fluid source 16 through the first pressure actuated valve 54a, thereby pulsing the fluid communication between the pressurized fluid source 16 and the aspiration flow path 46 at the first predetermined frequency; and conversely, configured for ceasing resonation in response to the prevention of the flow of fluid from the pressurized fluid source 16 through the first pressure actuated valve 54a.

The second pressure actuated valve 54b is configured for opening in response to a drop in absolute pressure in the aspiration flow path 28 that creates a second negative activation pressure differential between the inlet port 50 and the outlet port 52, thereby allowing a flow of fluid from the pressurized fluid source 16 through the second pressure actuated valve 54b; and conversely, for closing in response to an increase in absolute pressure in the aspiration flow path 28 that creates a second negative cessation pressure differential between the inlet port 50 and the outlet port 52, thereby preventing the flow of fluid from the pressurized fluid source 16 through the pressure actuated valve 54. The second fluid resonator 56b is configured for resonating at a second predetermined frequency in response to the flow of fluid from the pressurized fluid source 16 through the second pressure actuated valve 54b, thereby pulsing the fluid communication between the pressurized fluid source 16 and the aspiration flow path 46 at the second predetermined frequency; and conversely, configured for ceasing resonation in response to the prevention of the flow of fluid from the pressurized fluid source 16 through the second pressure actuated valve 54b.

The first and second negative activation pressure differentials may be the same (e.g., both indicating a clog in the aspiration conduit 24 of the aspiration catheter 12) or may be different (e.g., one indicating active thrombus ingestion into the aspiration catheter 12, and the other indicating clogging of the aspiration conduit 24 of the aspiration catheter 12). The first and second negative cessation pressure differentials may be the same (e.g., both indicating ingestion or removal of a clog in the aspiration conduit 24 of the aspiration catheter 12), although in alternative embodiments, the first and second negative cessation pressure differentials may be different. The first and second predetermined frequencies may be the same or may be different (e.g., one being a relatively high-frequency for disrupting a clogged thrombus 2 with a harder consistency, and the other being a relatively low-frequency for disrupting a clogged thrombus 2 with a softer consistency). The first pressure actuated valve 54a and the first fluid resonator 56a may be mechanically coupled to each other or mechanically decoupled from each other, and the second pressure actuated valve 54b and the second fluid resonator 56b may likewise be mechanically coupled to each other or mechanically decoupled from each other. Furthermore, the first pressure actuated valve 54*a* and the second pressure actuated valve 54*b* may be coupled to each other to essentially form a multi-outlet valve assembly that distributes flows to either one or the other or both of the fluid resonators 56*a*, 56*b* in response to various levels of a single sensed pressure differential.

Although the passive pressure oscillation assembly 44' is illustrated in FIG. 6 as comprising only two parallel sets of pressure actuated valve assemblies and fluid resonators, the passive pressure oscillation assembly 44' may alternatively comprise more than two parallel sets of pressure actuated valve assemblies and fluid resonators.

Figure 7:
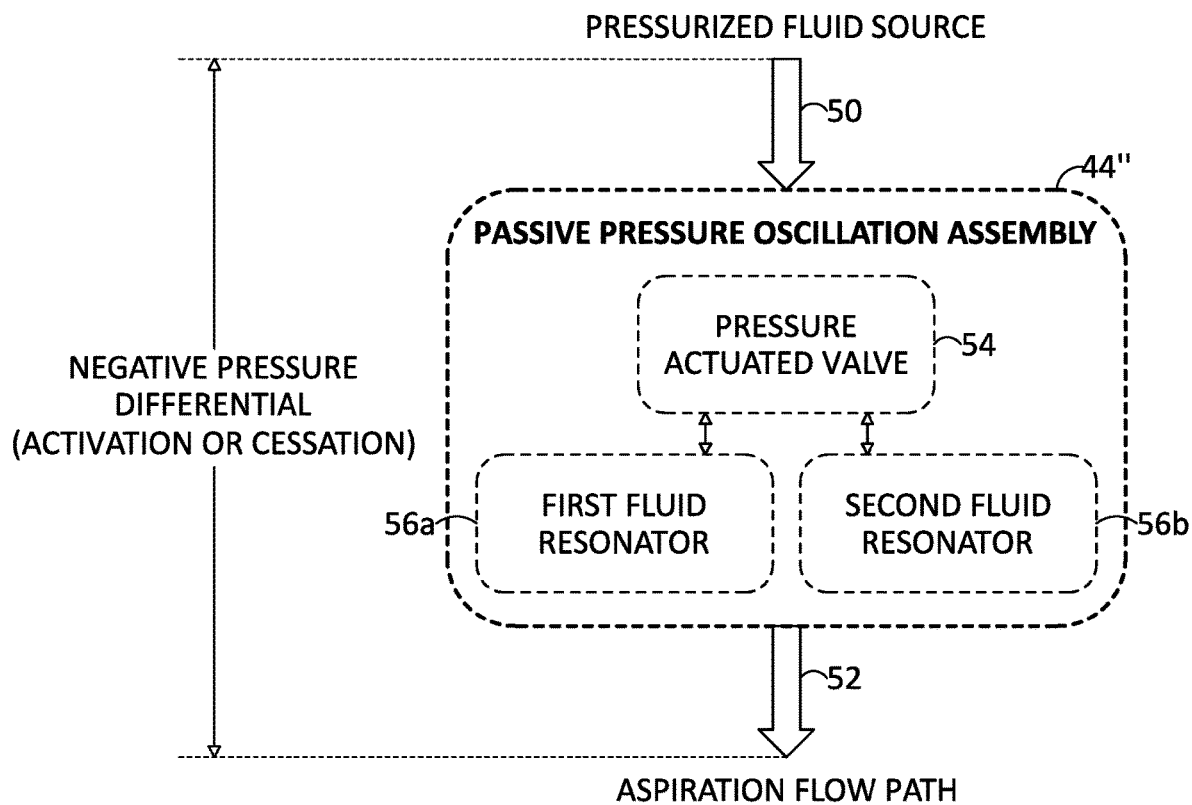
FIG. 7 is a block diagram of still another embodiment of a passive pressure oscillation assembly used in the aspiration system of FIG. 1.

Referring to FIG. 7, another alternative embodiment of a passive pressure oscillation assembly 44" comprises a single pressure actuated valve 54, a first fluid resonator 56*a*, and a second fluid resonator 56*b*.

The pressure actuated valve 54 is configured for opening in response to a drop in absolute pressure in the aspiration flow path 28 that creates a negative activation pressure differential between the inlet port 50 and the outlet port 52, thereby allowing the flow of fluid from the pressurized fluid source 16 through the first pressure actuated valve 54; and conversely, for closing in response to an increase in absolute pressure in the aspiration flow path 28 that creates a negative cessation pressure differential between the inlet port 50 and the outlet port 52 (e.g., indicative of the removal or clearance of a clog from the aspiration conduit 24 of the aspiration catheter 12), thereby preventing the flow of fluid from the pressurized fluid source 16 through the pressure actuated valve 54.

The first fluid resonator 56*a* is configured for resonating at a first predetermined frequency in response to the flow of fluid from the pressurized fluid source 16 through the pressure actuated valve 54, thereby pulsing the fluid communication between the pressurized fluid source 16 and the aspiration flow path 46 at the first predetermined frequency; and conversely, configured for ceasing resonation in response to the prevention of the flow of fluid from the pressurized fluid source 16 through the pressure actuated valve 54. The second fluid resonator 56*b* is configured for resonating at a second predetermined frequency in response to the flow of fluid from the pressurized fluid source 16 through the pressure actuated valve 54, thereby pulsing the fluid communication between the pressurized fluid source 16 and the aspiration flow path 46 at the second predetermined frequency; and conversely, configured for ceasing resonation in response to the prevention of the flow of fluid from the pressurized fluid source 16 through the pressure actuated valve 54.

The first and second predetermined frequencies may be the same or may be different (e.g., one being a relatively high-frequency for disrupting a clogged thrombus 2 with a harder consistency, and the other being a relatively low-frequency for disrupting a clogged thrombus 2 with a softer consistency). The first and second fluid resonators 56*a*, 56*b* may be mechanically decoupled from the pressure actuated valve 54.

Figure 8A:
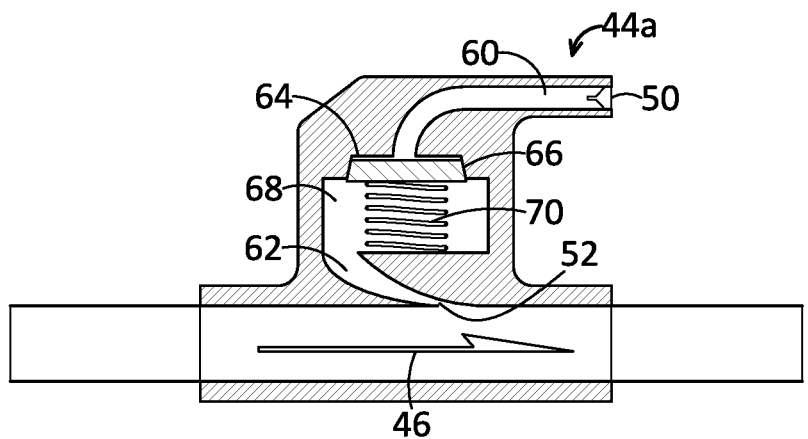
FIG. 8A is a plan view of one embodiment of a passive pressure oscillation assembly used in the aspiration system of FIG. 1, particularly showing the passive pressure oscillation assembly in a closed position.
Figure 8B:
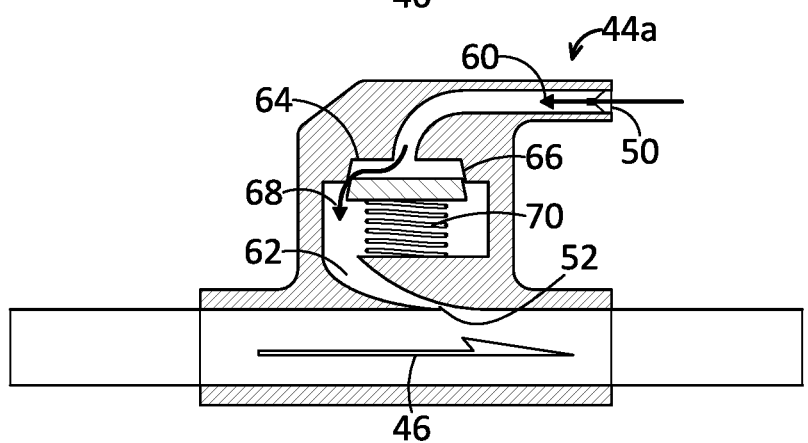
FIG. 8B is a plan view of the passive pressure oscillation assembly of FIG. 8A, particularly showing the passive pressure oscillation assembly in an open position.

Referring now to FIGS. 8A and 8B, one embodiment of a passive pressure oscillation assembly 44*a* will be described. The passive pressure oscillation assembly 44*a* comprises an inlet channel 60 fluidly coupled to the pressurized fluid source 16 via the inlet port 50, and an outlet channel 62 fluidly coupled to the aspiration flow path 46 via the outlet port 52. The passive pressure oscillation assembly 44*a* further comprises a valve seal in the form of a seat 64 fluidly coupled to the inlet port 50 via the inlet channel 60, a movable valve element in the form of a valve disk 66 operably associated with the valve seat 64, and an enlarged flow cavity 68 fluidly coupled between the valve seat 64 and the aspiration flow path 46 via the outlet channel 62 and outlet port 52. The valve disk 66 is configured for being alternately displaced between a closed position to seal against the valve seat 64, and in this case, within the valve seat 64 (see FIG. 8A), and an open position away from the valve seat 64, and in this case outside of the valve seat 64 (see FIG. 8B). The passive pressure oscillation assembly 44*a* further comprises a restoring spring 70 affixed within the enlarged flow cavity 68 and mechanically coupled to the valve disk 66 for applying a biasing force to the valve disk 66 in a manner that maintains the valve disk 66 in the closed position within the valve seat 64 until the passive pressure oscillation assembly 44*a* is triggered to switch from the normal mode to the oscillatory mode, as will be described in further detail below.

The valve disk 66 and valve seat 64 have the same geometric profile (in this case, a flattened trapezoidal shape cross-section), such that the valve disk 66, when in the closed position within the valve seat 64 (see FIG. 8A), seals against the valve seat 64 to prevent the flow of fluid originating from the pressurized fluid source 16 (in this case, fluid that has been introduced into the inlet channel 60 via the inlet port 50) into the enlarged flow cavity 68. The enlarged flow cavity 68 has a geometric profile that is larger than the geometric profile of the valve disk 66, such that the valve disk 66, when in the open position outside of the valve seat 64 and within the enlarged flow cavity 68 (see FIG. 8B), allows the flow of fluid originating from pressurized fluid source 16 (in this case, fluid that has been introduced into the inlet channel 60 via the inlet port 50), into the enlarged flow cavity 68, through the outlet channel 62, and into the aspiration flow path 46 via the outlet port 52.

In response to a clog in the aspiration conduit 24 of the aspiration catheter 12, or otherwise the occurrence of an anomaly in the aspiration circuit of the system 10, a no-flow or low-flow condition occurs in the aspiration flow path 46, and as a result, the absolute pressure in the aspiration flow path 46 drops to a level that creates a negative activation pressure differential between the inlet port 50 (and thus the inlet channel 60) and the outlet port 52 (and thus the enlarged flow cavity 68), which causes the fluid in the inlet channel 60 to apply an opposing force to the valve disk 66 that overcomes the biasing force applied by the restoring spring 70 to the valve disk 66. As a result, the valve disk 66 is displaced from the closed position (see FIG. 8A) to the open position (see FIG. 8B). The negative activation pressure differential of the passive pressure oscillation assembly 44*a* will be based on the area of the valve disk 66 exposed to the fluid in the inlet channel 60 (the negative activation pressure differential will decrease in proportion to the exposed area of the valve disk 66) and the spring constant of the restoring spring 70 (the negative action pressure differential will increase in proportion to the spring constant of the restoring spring 70). Thus, the negative activation pressure differential of the passive pressure oscillation assembly 44*a* may be selected by judicially selecting the exposed area of the valve disk 66 and the spring constant of the restoring spring 70.

The passive pressure oscillation assembly 44*a* is designed in such a manner that, once the valve disk 66 is displaced from the closed position to the open position (i.e., the valve "cracks"), the passive pressure oscillation assembly 44*a* resonates (i.e., the valve disk 66 alternately switches (oscillates) between the closed position and the open position. At this point, the passive pressure oscillation assembly 44a has been triggered to switch from the normal mode to the oscillatory mode.

In particular, the biasing force applied by the restoring spring 70 to the valve disk 66, the opposing force applied by the fluid in the inlet channel 60 to the valve disk 66, and the mass of the valve disk 66 are selected, such that the valve disk 66 oscillates between the closed position and the open position at a predetermined frequency (e.g., in the range of 100 Hz-400 Hz).

That is, when the valve disk 66 initially reaches the fully open position, the opposing force applied to the valve disk 66 by the fluid flowing from the inlet channel 60, through the valve seat 64, and into the enlarged flow cavity 68, drops to a level, such that the biasing force applied by the restoring spring 70 overcomes the opposing fluid force applied to the valve disk 66 and the momentum of the valve disk 66. As a result, the valve disk 66 is displaced from the open position back into the closed position within the valve seat 64 (see FIG. 8A). At this point, the momentary flow of fluid from the pressurized fluid source 16 into the aspiration flow path 46 (via the inlet port 50, inlet channel 60, valve seat 64, enlarged flow cavity 68, outlet channel 62, and outlet port 52), has caused the negative pressure differential between inlet port 50 and the outlet port 52 to increase. However, because the valve disk 66 is now in a closed position, thereby preventing the flow of fluid from the pressurized fluid source 16 to the aspiration flow path 46, the negative pressure differential between inlet port 50 and the outlet port 52 decreases until it reaches the negative activation pressure differential, causing the opposing force applied to the valve disk 66 by the fluid in the inlet channel 60 to rise to a level that overcomes the biasing force applied by the restoring spring 70 to the valve disk 66. As a result, the valve disk 66 is displaced from the closed position back to the open position (see FIG. 8B). The valve disk 66 continues to alternately be displaced between the closed position (see FIG. 8A) and the open position (see FIG. 8B) in this manner until the clog is removed from the aspiration conduit 24 of the aspiration catheter 12 or otherwise the anomaly in the aspiration circuit of the system 10 is resolved.

The frequency at which the valve disk 66 oscillates depends on the mass of the valve disk 66 (the frequency of the oscillation decreases as the mass of the valve disk 66 increases), the spring constant of the restoring spring 70 (the frequency of the oscillation increases as the spring constant of the restoring spring 70 increases), and the length of the valve seat 64 (the frequency of the oscillation increases as the length of the valve seat 64 decreases), as well as the dampening effect of the friction between the valve seat 64 and the valve disk 66 and the dynamic forces of the fluid flowing from the inlet channel 60, through the valve seat 64, and into the enlarged flow cavity 68, on the valve disk 66 (the frequency of the oscillation decreases as the dampening effect increases). Thus, the frequency at which the valve disk 66 oscillates (i.e., the resonance of the passive pressure oscillation assembly 44a) may be selected by judicially selecting the mass of the valve disk 66, spring constant of the restoring spring 70, length of the valve seat 64, and pre-compression length of the spring 70, with due regard to the dampening effect that the friction between the valve seat 64 and the valve disk 66 and the fluid flow associated pressure drop from the inlet channel 60, through the valve seat 64, and into the enlarged flow cavity 68, has on the valve disk 66. Such dampening effect, itself, may be adjusted by varying the designed sizes and geometries of the inlet port 50, outlet port 52, inlet channel 60, and outlet channel 62.

In response to removal of the clog in the aspiration conduit 24 of the aspiration catheter 12, or otherwise the resolution of the anomaly in the aspiration circuit of the system 10, the absolute pressure in the aspiration flow path 46 increases to a level that creates a negative cessation pressure differential between the inlet port 50 (and thus the inlet channel 60) and the outlet port 52 (and thus the enlarged flow cavity 68), which prevents the fluid in the inlet channel 60 from applying an opposing force to the valve disk 66 that overcomes the biasing force applied by the restoring spring 70 to the valve disk 66. That is, when the valve disk 66 is in the closed position, the negative pressure differential between inlet port 50 and the outlet port 52 will never drop below the negative activation pressure differential due to the free flow condition of the aspiration flow path 46. As a result, the biasing force applied by the restoring spring 70 maintains the valve disk 66 in the closed position. At this point, the passive pressure oscillation assembly 44a has been triggered to switch from the oscillatory mode back to the normal mode.

It should be noted that the passive pressure oscillation assembly 44a illustrated in FIGS. 8A and 8B topologically comprises a pressure actuated valve 54 and a fluid resonator 56 (shown in FIG. 5) that are mechanically coupled to each other. That is, the valve seat 64 and movable valve disk 66 form the pressure actuated valve 54, whereas the valve disk 66, enlarged flow cavity 68, and restoring spring 70 form the fluid resonator 56, with the pressure actuated valve 54 and fluid resonator 56 being mechanically coupled to each other via the valve disk 66. In this embodiment, because the valve disk 66 forms a portion of both the pressure actuated valve 54 and the fluid resonator 56, the negative activation and cessation pressure differentials and the resonance frequency must be designed with due regard to each other, and thus, may not be able to be independently optimized, although the resulting design of the passive pressure oscillation assembly 44a may be mechanically simple.

Figure 9A:
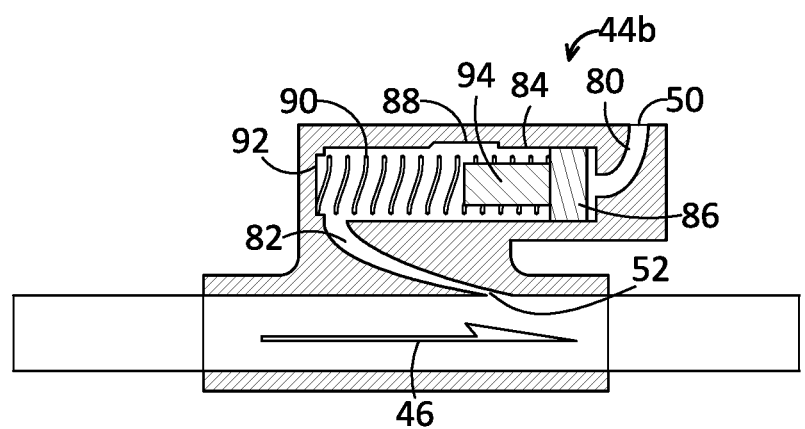
FIG. 9A is a plan view of another embodiment of a passive pressure oscillation assembly used in the aspiration system of FIG. 1, particularly showing the passive pressure oscillation assembly in a closed position.
Figure 9B:
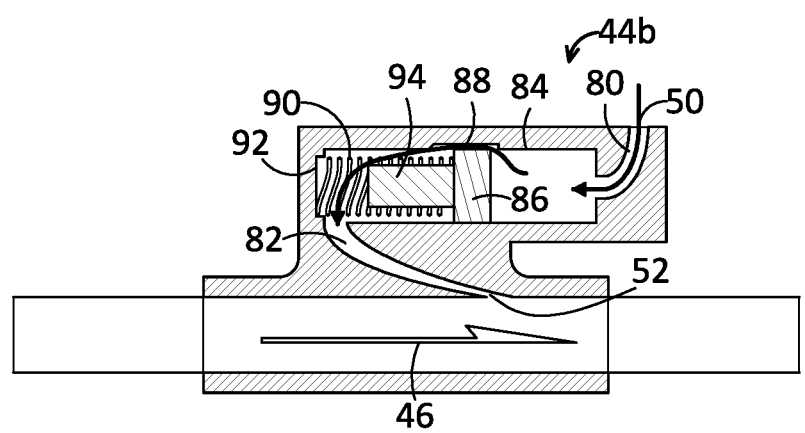
FIG. 9B is a plan view of the passive pressure oscillation assembly of FIG. 9A, particularly showing the passive pressure oscillation assembly in an open position.
Figure 10A:
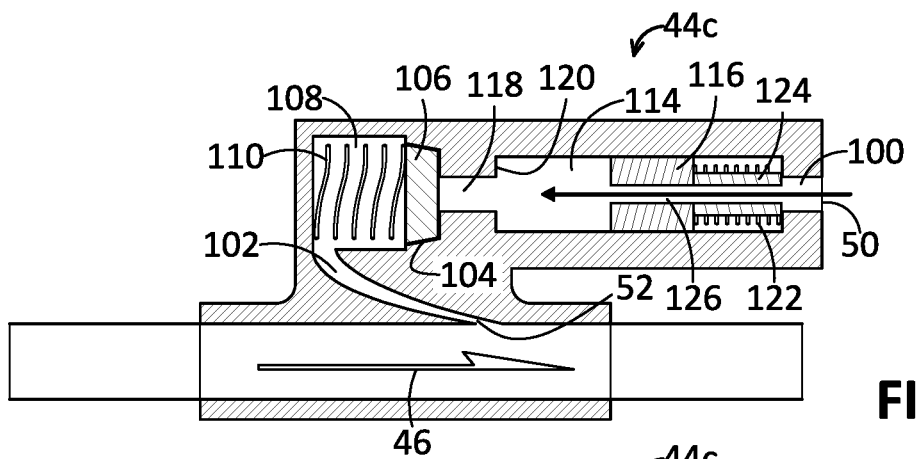
FIG. 10A is a plan view of another embodiment of a passive pressure oscillation assembly used in the aspiration system of FIG. 1, particularly showing the passive pressure oscillation assembly in a first state.
Figure 10B:
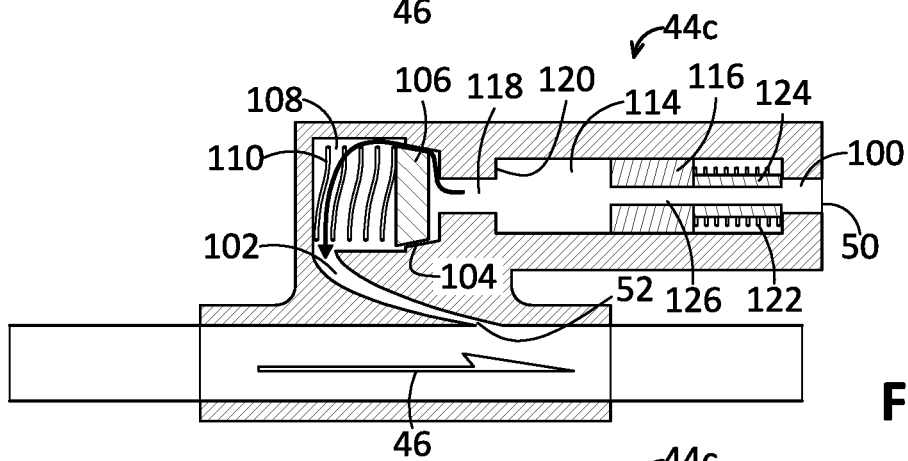
FIG. 10B is a plan view of the passive pressure oscillation assembly of FIG. 10A, particularly showing the passive pressure oscillation assembly in a second state.
Figure 10C:
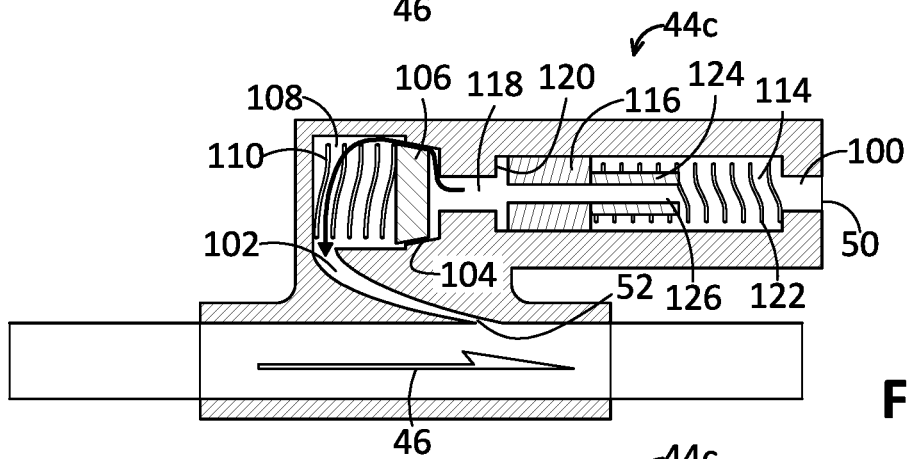
FIG. 10C is a plan view of the passive pressure oscillation assembly of FIG. 10A, particularly showing the passive pressure oscillation assembly in a third state.
Figure 10D:
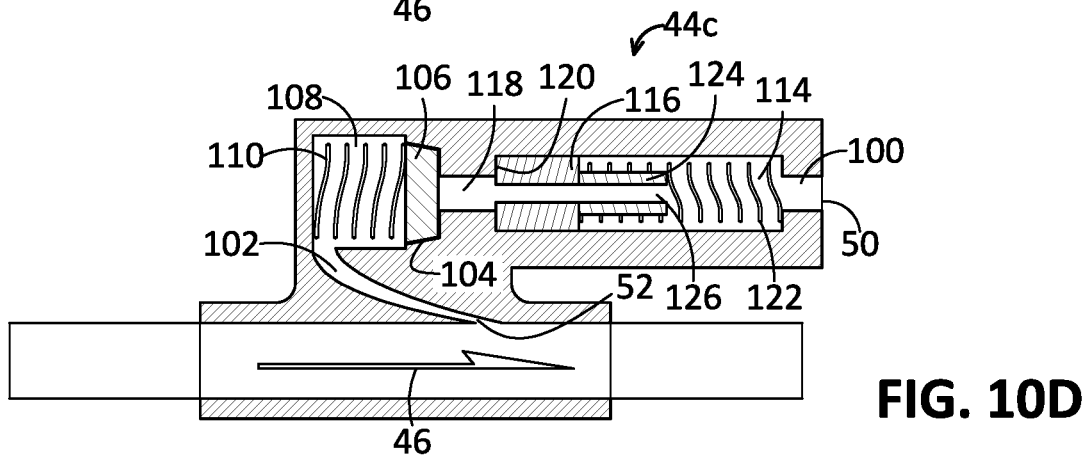
FIG. 10D is a plan view of the passive pressure oscillation assembly of FIG. 10A, particularly showing the passive pressure oscillation assembly in a fourth state.

Referring now to FIGS. 9A and 9B, another embodiment of a passive pressure oscillation assembly 44b will be described. The passive pressure oscillation assembly 44b is similar to the passive pressure oscillation assembly 44a illustrated in FIGS. 8A and 8B, with the exception that the passive pressure oscillation assembly 44b comprises a long valve seal relative to the movable valve element in which it interacts, such that its resonant frequency is much slower than that of the passive pressure oscillation assembly 44a.

In particular, passive pressure oscillation assembly 44b comprises an inlet channel 80 fluidly coupled to the pressurized fluid source 16 via the inlet port 50, and an outlet channel 82 fluidly coupled to the aspiration flow path 46 via the outlet port 52. The passive pressure oscillation assembly 44b further comprises a valve seal in the form of a valve cylinder 84 fluidly coupled to the inlet port 50 via the inlet channel 80, a movable valve element in the form of a valve disk 86 operatively associated with the valve cylinder 84, and an enlarged flow cavity 88 fluidly coupled between the valve cylinder 84 and the aspiration flow path 46 via the outlet channel 62 and outlet port 52. The valve disk 86 is configured for being alternately displaced between a closed position to seal within the valve cylinder 84 (see FIG. 9A), and an open position residing within the enlarged flow cavity 88 (see FIG. 9B). The passive pressure oscillation assembly 44b further comprises a restoring spring 90 disposed in a spring cavity 92 between the enlarged flow cavity 88 and the outlet channel 82, and mechanically coupled to the valve disk 86 via a boss 94 affixed to the valve disk 86 for applying a biasing force to the valve disk 86 in a manner that maintains the valve disk 86 into the closed position within the valve cylinder 84 until the passive pressure oscillation assembly 44b is triggered to switch from the normal mode to the oscillatory mode.

The valve disk 86 and valve cylinder 84 have the same geometric profile (in this case, a cylindrical in nature), such that the valve disk 86, when in the closed position within the valve cylinder 84 (see FIG. 9A), seals against the valve cylinder 84 to prevent the flow of fluid originating from the pressurized fluid source 16 (in this case, fluid that has been introduced into the inlet channel 80 via the inlet port 50) into the enlarged flow cavity 88. The enlarged flow cavity 88 has a geometric profile that is larger than the geometric profile of the valve disk 86, such that the valve disk 86, when in the open position outside of the valve cylinder 84 and within the enlarged flow cavity 88 (see FIG. 9B), allows the flow of fluid originating from pressurized fluid source 16 (in this case, fluid that has been introduced into the inlet channel 80 via the inlet port 50), into the enlarged flow cavity 88, through the outlet channel 82, and into the aspiration flow path 46 via the outlet port 52.

In response to a clog in the aspiration conduit 24 of the aspiration catheter 12, or otherwise the occurrence of an anomaly in the aspiration circuit of the system 10, a no-flow or low-flow condition occurs in the aspiration flow path 46, and as a result, the absolute pressure in the aspiration flow path 46 drops to a level that creates a negative activation pressure differential between the inlet port 50 (and thus the valve cylinder 84) and the outlet port 52 (and thus the enlarged flow cavity 88), which causes the fluid in the inlet channel 80 to apply an opposing force to the valve disk 86 that overcomes the biasing force applied by the restoring spring 90 to the valve disk 86. As a result, the valve disk 86 is displaced from the closed position (see FIG. 9A) to the open position (see FIG. 9B). The negative activation pressure differential of the passive pressure oscillation assembly 44b will be based on the area of the valve disk 86 exposed to the fluid in the valve cylinder 84 (the negative activation pressure differential will decrease in proportion to the exposed area of the valve disk 86) and the spring constant of the restoring spring 90 (the negative action pressure differential will increase in proportion to the spring constant of the restoring spring 90). Thus, the negative activation pressure differential of the passive pressure oscillation assembly 44b may be selected by judicially selecting the exposed area of the valve disk 86 and the spring constant of the restoring spring 90.

The passive pressure oscillation assembly 44b is designed in such a manner that, once the valve disk 86 is displaced from the closed position to the open position (i.e., the valve "cracks"), the passive pressure oscillation assembly 44b resonates (i.e., the valve disk 86 alternately switches (oscillates) between the closed position and the open position. At this point, the passive pressure oscillation assembly 44b has been triggered to switch from the normal mode to the oscillatory mode.

In particular, the biasing force applied by the restoring spring 90 to the valve disk 86, the opposing force applied by the fluid in the valve cylinder 84, and the mass of the valve disk 86 are selected, such that the valve disk 86 oscillates between the closed position and the open position at a predetermined frequency (e.g., in the range of 100 Hz-200 Hz).

That is, when the valve disk 86 fully reaches the open position, the opposing force applied to the valve disk 86 by the fluid flowing from the inlet channel 80, through the valve cylinder 84, and into the enlarged flow cavity 88, drops to a level, such that the biasing force applied by the restoring spring 90 overcomes the opposing fluid force applied to the valve disk 86 and the momentum of the valve disk 86. As a result, the valve disk 86 is displaced from the open position back into the closed position within the valve cylinder 84 (see FIG. 9A). At this point, the momentary flow of fluid from the pressurized fluid source 16 into the aspiration flow path 46 (via the inlet port 50, inlet channel 80, valve cylinder 84, enlarged flow cavity 88, spring cavity 92, outlet channel 82, and outlet port 52), has caused the negative pressure differential between inlet port 50 and the outlet port 52 to increase. However, because the valve disk 86 is now in a closed position, thereby preventing the flow of fluid from the pressurized fluid source 16 to the aspiration flow path 46, the negative pressure differential between inlet port 50 and the outlet port 52 decreases until it reaches the negative activation pressure differential, causing the opposing force applied to the valve disk 86 by the fluid in the valve cylinder 84 to rise to a level that overcomes the biasing force applied by the restoring spring 90 to the valve disk 86. As a result, the valve disk 86 is again displaced from the closed position to the open position (see FIG. 9B). The valve disk 86 continues to alternately be displaced between the closed position (see FIG. 9A) and the open position (see FIG. 9B) in this manner until the clog is removed from the aspiration catheter 12 or otherwise the anomaly in the aspiration circuit of the system 10 is resolved.

The frequency at which the valve disk 86 oscillates depends on the mass of the valve disk 86 (the frequency of the oscillation decreases as the mass of the valve disk 86 increases), the spring constant of the restoring spring 90 (the frequency of the oscillation increases as the spring constant of the restoring spring 90 increases), and the length of the valve cylinder 84 (the frequency of the oscillation increases as the length of the valve seat 64 decreases), as well as the dampening effect of the friction between the valve cylinder 84 and the valve disk 86 and the dynamic forces of the fluid flowing from the inlet channel 60, through the valve cylinder 84, and into the enlarged flow cavity 88, on the valve disk 86 (the frequency of the oscillation decreases as the dampening effect increases). Thus, frequency at which the valve disk 86 oscillates (i.e., the resonance of the passive pressure oscillation assembly 44b) may be selected by judicially selecting the mass of the valve disk 86 and the spring constant of the restoring spring 90, length of the valve cylinder 84, and pre-compression length of the spring 90, with due regard to the dampening effect that the friction between the valve cylinder 84 and the valve disk 86 and the fluid flowing from the inlet channel 80, through the valve cylinder 84, and into the enlarged flow cavity 88, has on the valve disk 86. Such dampening effect, itself, may be adjusted by varying the designed sizes and geometries of the inlet port 50, outlet port 52, inlet channel 80, and outlet channel 82.

In response to removal of the clog in the aspiration conduit 24 of the aspiration catheter 12, or otherwise the resolution of the anomaly in the aspiration circuit of the system 10, the absolute pressure in the aspiration flow path 46 increases to a level that creates a negative activation pressure differential between the inlet port 50 (and thus the valve cylinder 84) and the outlet port 52 (and thus the enlarged flow cavity 88), which prevents the fluid in the inlet channel 80 from applying an opposing force to the valve disk 86 that overcomes the biasing force applied by the restoring spring 90 to the valve disk 86. That is, when the movable valve cylinder 86 is in the closed position, the negative pressure differential between inlet port 50 and the outlet port 52 will never drop below the negative activation pressure differential due to the free flow condition of the aspiration flow path 46. As a result, the biasing force applied by the restoring spring 90 maintains the valve disk 86 in the closed position. At this point, the passive pressure oscillation assembly 44b has been triggered to switch from the oscillatory mode to the normal mode.

It should be noted that the passive pressure oscillation assembly 44b illustrated in FIGS. 9A and 9B topologically comprises a pressure actuated valve 54 and a fluid resonator 56 (shown in FIG. 5) that are mechanically coupled to each other. That is, the valve cylinder 84 and valve disk 86 form the pressure actuated valve 54, whereas the valve disk 86, enlarged flow cavity 88, and restoring spring 90 form the fluid resonator 56, with the pressure actuated valve 54 and fluid resonator 56 being mechanically coupled to each other via the valve disk 86. In this embodiment, because the valve disk 86 forms a portion of both the pressure actuated valve 54 and the fluid resonator 56, the negative activation and cessation pressure differentials and the resonance frequency must be designed with due regard to each other, and thus, may not be able to be independently optimized, although the resulting design of the passive pressure oscillation assembly 44b may be mechanically simple.

Referring now to FIGS. 10A-10D, still another embodiment of a passive pressure oscillation assembly 44c will be described. The passive pressure oscillation assembly 44c is similar to the passive pressure oscillation assembly 44a illustrated in FIGS. 6A and 6B, with the exception that the passive pressure oscillation assembly 44c comprises an additional oscillation enhancement mechanism that ensures that the passive pressure oscillation assembly 44c remains in the oscillatory mode as long as the clog in the aspiration conduit 24 of the aspiration catheter 12 remains, or otherwise the anomaly in the aspiration circuit of the system 10 is not resolved.

The passive pressure oscillation assembly 44c comprises an inlet channel 100 fluidly coupled to the pressurized fluid source 16 via the inlet port 50, and an outlet channel 102 fluidly coupled to the aspiration flow path 46 via the outlet port 52. The passive pressure oscillation assembly 44c further comprises a valve seal in the form of a seat 104, a movable valve element in the form of a valve disk 106 operably associated with the valve seat 104, and an enlarged flow cavity 108 that fluidly couples the valve seat 104 to the aspiration flow path 46 via the outlet channel 102 and outlet port 52. The valve disk 106 is configured for being alternately displaced between a closed position to seal against the valve seat 104, and in this case, within the valve seat 104 (see FIGS. 10A and 10D), and an open position away from the valve seat 104, and in this case outside of the valve seat 104 (see FIGS. 10B and 10C). The passive pressure oscillation assembly 44c further comprises a restoring spring 110 disposed in the enlarged flow cavity 108 and mechanically coupled to the valve disk 106 for applying a biasing force to the valve disk 106 in a manner that maintains the valve disk 106 into the closed position within the valve seat 104 until the passive pressure oscillation assembly 44c is triggered to switch from the normal mode to the oscillatory mode.

The passive pressure oscillation assembly 44c further comprises a plunger cavity 114, a plunger head 116 slidably disposed within the plunger cavity 114, a reduced profile center cavity 118, a plunger stop 120 disposed between the plunger cavity 114 and the reduced profile center cavity 118, and another restoring spring 122 mechanically coupled to the plunger head 116 via a boss 124 affixed to the plunger head 116 for applying a biasing force to the plunger head 116 to maintain the plunger head 116 away from the plunger stop 120. In the illustrated embodiment, the profile of the reduced profile center cavity 118 is smaller than the profile of the plunger cavity 114, such that the plunger stop 120 is formed by the wall of the plunger cavity 114 adjacent the reduced profile center cavity 118. The plunger head 116 has a fluid pressure equalization channel 126 extending through the plunger head 116. The plunger cavity 114 is fluidly coupled between the valve seat 104 and the plunger cavity 114, such that the valve seat 104 is always in fluid communication with the inlet port 50 via the fluid pressure equalization channel 126 extending through the plunger head 116, and fluid originating from the pressurized fluid source 16 can flow into the reduced profile center cavity 118. Thus, the fluid pressure equalization channel 126 extending through the plunger head 116 serves to equalize the pressure between the pressurized fluid source 16 and the reduced profile center cavity 118.

The valve disk 106 and valve seat 104 have the same geometric profile (in this case, a flattened trapezoidal shape cross-section), such that the valve disk 106, when in the closed position within the valve seat 104 (see FIGS. 10A and 10D), prevents the flow of fluid originating from the pressurized fluid source 16 (in this case, fluid that has been introduced into the reduced profile center cavity 118 from the inlet channel 100 via the inlet port 50, and through the fluid pressure equalization channel 126 of the plunger head 116) into the enlarged flow cavity 108. The enlarged flow cavity 108 has a geometric profile that is larger than the geometric profile of the valve disk 106, such that the valve disk 106, when in the open position outside of the valve seat 104 and inside the enlarged flow cavity 108 (see FIGS. 10B and 10C), allows the flow of fluid originating from pressurized fluid source 16 (in this case, fluid that has been introduced into plunger cavity 114 from the inlet port 50 and the inlet channel 100 via the fluid pressure equalization channel 126), into the enlarged flow cavity 108, through the outlet channel 102, and into the aspiration flow path 46 via the outlet port 52. The plunger head 116 and plunger cavity 114 have the same geometric profile (in this case, a cylindrical in nature), such fluid from the pressurized fluid source 16 can only enter the reduced profile center cavity 118 via the fluid pressure equalization channel 126 of the plunger head 116.

In response to a clog in the aspiration conduit 24 of the aspiration catheter 12, or otherwise the occurrence of an anomaly in the aspiration circuit of the system 10, a no-flow or low-flow condition occurs in the aspiration flow path 46, and as a result, the absolute pressure in the aspiration flow path 46 drops to a level that creates a negative activation pressure differential between the inlet port 50 (and thus the reduced profile center cavity 118) and the outlet port 52 (and thus the enlarged flow cavity 108), which causes the fluid in the plunger cavity 114, and thus reduced profile center cavity 118, to apply an opposing force to the valve disk 106 that overcomes the biasing force applied by the restoring spring 110 to the valve disk 106. As a result, the valve disk 106 is displaced from the closed position (see FIG. 10A) to the open position (see FIG. 10B). The negative activation pressure differential of the passive pressure oscillation assembly 44c will be based on the area of the valve disk 106 exposed to the fluid in the inlet channel 100 (the negative activation pressure differential will decrease in proportion to the exposed area of the valve disk 106) and the spring constant of the restoring spring 110 (the negative action pressure differential will increase in proportion to the spring constant of the restoring spring 110). Thus, the negative activation pressure differential of the passive pressure oscillation assembly 44c may be selected by judicially selecting the exposed area of the valve disk 106 and the spring constant of the restoring spring 110.

The passive pressure oscillation assembly 44c is designed in such a manner that, once the valve disk 106 is displaced from the closed position to the open position (i.e., the valve "cracks"), the passive pressure oscillation assembly 44c resonates (i.e., the valve disk 106 alternately switches (oscillates) between the closed position and the open position. At this point, the passive pressure oscillation assembly 44c has been triggered to switch from the normal mode to the oscillatory mode.

In particular, the biasing force applied by the restoring spring 110 to the valve disk 106, the opposing force applied by the fluid in the reduced profile center cavity 118 to the valve disk 106, and mass of the valve disk 106 are selected, such that the valve disk 106 oscillates between the closed position and the open position at a predetermined frequency. Furthermore, dynamic displacement of the plunger head 116 within the plunger cavity 114 ensures that the valve disk 106 does not get stuck in the open position as the fluid flowing from the reduced profile center cavity 118 into the enlarged flow cavity 108 applies a force to the valve disk 106.

In particular, as the valve disk 106 is displaced from the closed position to the open position (see FIG. 10C), fluid flows from the plunger cavity 114 in front of the plunger head 116, through the reduced profile center cavity 118, through the valve seat 104, and into the enlarged flow cavity 108, causing the plunger head 116 to be displaced within the plunger cavity 114 towards the reduced profile center cavity 118 until the plunger head 116 abuts the plunger stop 120, and additional fluid to flow from the pressurized fluid source 16 into the plunger cavity 114 behind the plunger head 116 via the inlet port 50 and inlet channel 100. Once the plunger head 116 abuts the plunger stop 120, the flow of fluid from the reduced profile center cavity 118, through the valve seat 104, and into the enlarged flow cavity 108 is greatly diminished, limited to the flow of fluid through the fluid pressure equalization channel 126 through the plunger head 116. Thus, the opposing force applied to the valve disk 106 by the fluid flowing from the reduced profile center cavity 118, through the valve seat 104, and into the enlarged flow cavity 108, drops to a level, such that the biasing force applied by the restoring spring 110 overcomes the opposing fluid force applied to the valve disk 106 and the momentum of the valve disk 106. As a result, the valve disk 106 is displaced from the open position back into the closed position within the valve seat 104 (see FIG. 10D). The fluid pressure between the reduced profile center cavity 118 and the plunger cavity 114 equalizes via the fluid pressure equalization channel 126 through the plunger head 116, thereby dropping the opposing force applied to the plunger head 116 by the fluid in the plunger cavity 114 to a level, such that the biasing force applied by the restoring spring 122 overcomes the opposing fluid force applied to the plunger head 116 and the momentum of the plunger head 116. As a result, the plunger head 116 is displaced within the plunger cavity 114 away from the plunger stop 120, and returns to its neutral position (see FIG. 10A). In this manner, in contrast to the passive pressure oscillation assembly 44a illustrated in FIGS. 8A-8B, as well as the passive pressure oscillation assembly 44a illustrated in FIGS. 9A-9B, where fluid flows through the valve seat unimpeded, which under certain circumstances, may cause the valve disk to remain open, thereby preventing oscillation of the valve seat between the closed and open positions, the action of the plunger head 116 within the plunger cavity 114 prevents the valve disk 106 from "sticking" in the open position by greatly diminishing the flow of fluid through the valve seat 104 that might otherwise prevent the valve disk 106 to revert back to its closed position within the valve seat 104.

The frequency at which the valve disk 106 oscillates depends on the frequency at which the plunger head 116 oscillates within the plunger cavity 114, which in turn, depends on the mass of the plunger head 116 (the frequency of the oscillation decreases as the mass of the plunger head 116 increases), the spring constant of the restoring spring 122 (the frequency of the oscillation increases as the spring constant of the restoring spring 122 increases), the diameter of the equalization channel 126, and the dampening effect of the friction between the plunger cavity 114 and the plunger head 116, as well as dynamic forces of the fluid within the plunger cavity 114, including the fluid flowing through the channel fluid pressure equalization channel 126 of the plunger head 116 during equalization of the fluid pressure in the plunger cavity 114 (the frequency of the oscillation decreases as the dampening effect increases). Thus, frequency at which the valve disk 106 oscillates (i.e., the resonance of the passive pressure oscillation assembly 44c) may be selected by judicially selecting the mass of the plunger head 116 and the spring constant of the restoring spring 122, and the diameter of the equalization channel 126, with due regard to the dampening effect that the friction between the plunger cavity 114 and the plunger head 116, and the dynamics of the fluid within the reduced profile center cavity 118, have on the plunger head 116. Such dampening effect, itself, may be adjusted by varying the designed size of the inlet port 50, outlet port 52, inlet channel 100, and outlet channel 102.

In response to removal of the clog in the aspiration conduit 24 of the aspiration catheter 12, or otherwise the resolution of the anomaly in the aspiration circuit of the system 10, the absolute pressure in the aspiration flow path 46 increases to a level that creates a negative cessation pressure differential between the inlet port 50 (and thus the inlet channel 100) and the outlet port 52 (and thus the enlarged flow cavity 108), which prevents the fluid in the reduced profile center cavity 118 from applying an opposing force to the valve disk 106 that overcomes the biasing force applied by the spring 100 to the valve disk 106. That is, when the valve disk 106 is in the closed position, the negative pressure differential between inlet port 50 and the outlet port 52 will never drop below the negative activation pressure differential due to the free flow condition of the aspiration flow path 46. As a result, the biasing force applied by the restoring spring 110 maintains the valve disk 106 in the closed position. At this point, the passive pressure oscillation assembly 44c has been triggered to switch from the oscillatory mode to the normal mode.

Although the movable valve elements in the passive pressure oscillation assemblies 44a-44c illustrated in FIGS. 8-10 have been described as being valve disks, it should be appreciated that the movable valve elements may have any suitable form that can be operatively associated with a corresponding valve seal for alternately allowing and preventing the flow of fluid originating from the pressurized fluid source 16 therethrough. For example, with reference to FIGS. 11A and 11B, an alternative embodiment of a passive pressure oscillation assembly 44d is similar to the passive pressure oscillation assembly 44a of FIGS. 8A-8B, with the exception that the movable valve element takes the form of a ball.

In particular, the passive pressure oscillation assembly 44*d* comprises a comprises an inlet channel 130 fluidly coupled to the pressurized fluid source 16 via the inlet port 50, and an outlet channel 132 fluidly coupled to the aspiration flow path 46 via the outlet port 52. The passive pressure oscillation assembly 44*d* further comprises a valve seal in the form of a seat 134 fluidly coupled to the inlet port 50 via the inlet channel 130, a movable valve element in the form of a valve ball 136 operably associated with the valve seat 134, and an enlarged flow cavity 138 fluidly coupled between the valve seat 134 and the aspiration flow path 46 via the outlet channel 132 and outlet port 52. The valve ball 136 is configured for being alternately displaced between a closed position to seal against the valve seat 134 (see FIG. 11A), and an open position away from the valve seat 64, and in this case outside of the valve seat 64 (see FIG. 11B). The passive pressure oscillation assembly 44*d* further comprises a spring 140 affixed within the enlarged flow cavity 138 and mechanically coupled to the valve ball 136 for applying a biasing force to the valve ball 136 in a manner that maintains the valve ball 136 in the closed position against valve seat 134 until the passive pressure oscillation assembly 44*d* is triggered to switch from the normal mode to the oscillatory mode, as will be described in further detail below.

The surface of the valve seat 134 that contacts the valve ball 136 preferably has a spherical profile, such that the valve ball 136, when in the closed position against the valve seat 134 (see FIG. 11A), seals against the valve seat 134 to prevent the flow of fluid originating from the pressurized fluid source 16 (in this case, fluid that has been introduced into the inlet channel 130 via the inlet port 50) into the enlarged flow cavity 138. The enlarged flow cavity 138 has a geometric profile that is larger than the geometric profile of the valve ball 136, such that the valve ball 136, when in the open position away from the valve seat 134 and within the enlarged flow cavity 138 (see FIG. 11B), allows the flow of fluid originating from pressurized fluid source 16 (in this case, fluid that has been introduced into the inlet channel 130 via the inlet port 50), into the enlarged flow cavity 138, through the outlet channel 132, and into the aspiration flow path 46 via the outlet port 52.

In response to a clog in the aspiration conduit 24 of the aspiration catheter 12, or otherwise the occurrence of an anomaly in the aspiration circuit of the system 10, a no-flow or low-flow condition occurs in the aspiration flow path 46, and as a result, the absolute pressure in the aspiration flow path 46 drops to a level that creates a negative activation pressure differential between the inlet port 50 (and thus the inlet channel 130) and the outlet port 52 (and thus the enlarged flow cavity 138), which causes the fluid in the inlet channel 130 to apply an opposing force to the valve ball 136 that overcomes the biasing force applied by the spring 140 to the valve ball 136. As a result, the valve ball 136 is displaced from the closed position (see FIG. 11A) to the open position (see FIG. 11B). The negative activation pressure differential of the passive pressure oscillation assembly 44*d* will be based on the area of the valve ball 136 exposed to the fluid in the inlet channel 130 (the negative activation pressure differential will decrease in proportion to the exposed area of the valve ball 136) and the spring constant of the spring 140 (the negative action pressure differential will increase in proportion to the spring constant of the spring 140). Thus, the negative activation pressure differential of the passive pressure oscillation assembly 44*d* may be selected by judicially selecting the exposed area of the valve ball 136 and the spring constant of the spring 140.

The passive pressure oscillation assembly 44*d* is designed in such a manner that, once the valve ball 136 is displaced from the closed position to the open position (i.e., the valve "cracks"), the passive pressure oscillation assembly 44*d* resonates (i.e., the valve ball 136 alternately switches (oscillates) between the closed position and the open position. At this point, the passive pressure oscillation assembly 44*d* has been triggered to switch from the normal mode to the oscillatory mode.

In particular, the biasing force applied by the spring 140 to the valve ball 136, the opposing force applied by the fluid in the inlet channel 130 to the valve ball 136, and the mass of the valve ball 136 are selected, such that the valve ball 136 oscillates between the closed position and the open position at a predetermined frequency (e.g., 320 Hz-400 Hz).

That is, when the valve ball 136 initially reaches the fully open position, the opposing force applied to the valve ball 136 by the fluid flowing from the inlet channel 60, through the valve seat 134, and into the enlarged flow cavity 138, drops to a level, such that the biasing force applied by the spring 140 overcomes the opposing fluid force applied to the valve ball 136 and the momentum of the valve ball 136. As a result, the valve ball 136 is displaced from the open position back into the closed position within the valve seat 134 (see FIG. 11A). At this point, the momentary flow of fluid from the pressurized fluid source 16 into the aspiration flow path 46 (via the inlet port 50, inlet channel 130, valve seat 134, enlarged flow cavity 138, outlet channel 132, and outlet port 52), has caused the negative pressure differential between inlet port 50 and the outlet port 52 to increase. However, because the valve ball 136 is now in a closed position, thereby preventing the flow of fluid from the pressurized fluid source 16 to the aspiration flow path 46, the negative pressure differential between inlet port 50 and the outlet port 52 decreases until it reaches the negative activation pressure differential, causing the opposing force applied to the valve ball 136 by the fluid in the inlet channel 60 to rise to a level that overcomes the biasing force applied by the spring 140 to the valve ball 136. As a result, the valve ball 136 is displaced from the closed position back to the open position (see FIG. 11B). The valve ball 136 continues to alternately be displaced between the closed position (see FIG. 11A) and the open position (see FIG. 11B) in this manner until the clog is removed from the aspiration conduit 24 of the aspiration catheter 12 or otherwise the anomaly in the aspiration circuit of the system 10 is resolved.

The frequency at which the valve ball 136 oscillates depends on the mass of the valve ball 136 (the frequency of the oscillation decreases as the mass of the valve ball 136 increases), and the spring constant of the spring 140 (the frequency of the oscillation increases as the spring constant of the spring 140 increases), as well as the dampening effect of the dynamic forces of the fluid flowing from the inlet channel 130, through the valve seat 134, and into the enlarged flow cavity 138, on the valve ball 136 (the frequency of the oscillation decreases as the dampening effect increases). Thus, the frequency at which the valve ball 136 oscillates (i.e., the resonance of the passive pressure oscillation assembly 44*a*) may be selected by judicially selecting the mass of the valve ball 136, spring constant of the spring 140, length of the valve seat 134, and pre-compression length of the spring 140, with due regard to the dampening effect that the fluid flowing from the inlet channel 130, through the valve seat 134, and into the enlarged flow cavity 138, has on the valve ball 136. Such dampening effect, itself, may be adjusted by varying the designed sizes and geometries of the inlet port 50, outlet port 52, inlet channel 130, and outlet channel 132.

In response to removal of the clog in the aspiration conduit 24 of the aspiration catheter 12, or otherwise the resolution of the anomaly in the aspiration circuit of the system 10, the absolute pressure in the aspiration flow path 46 increases to a level that creates a negative cessation pressure differential between the inlet port 50 (and thus the inlet channel 130) and the outlet port 52 (and thus the enlarged flow cavity 138), which prevents the fluid in the inlet channel 130 from applying an opposing force to the valve ball 136 that overcomes the biasing force applied by the spring 140 to the valve ball 136. That is, when the valve ball 136 is in the closed position, the negative pressure differential between inlet port 50 and the outlet port 52 will never drop below the negative activation pressure differential due to the free flow condition of the aspiration flow path 46. As a result, the biasing force applied by the spring 140 maintains the valve ball 136 in the closed position. At this point, the passive pressure oscillation assembly 44*d* has been triggered to switch from the oscillatory mode back to the normal mode.

Figure 11A:
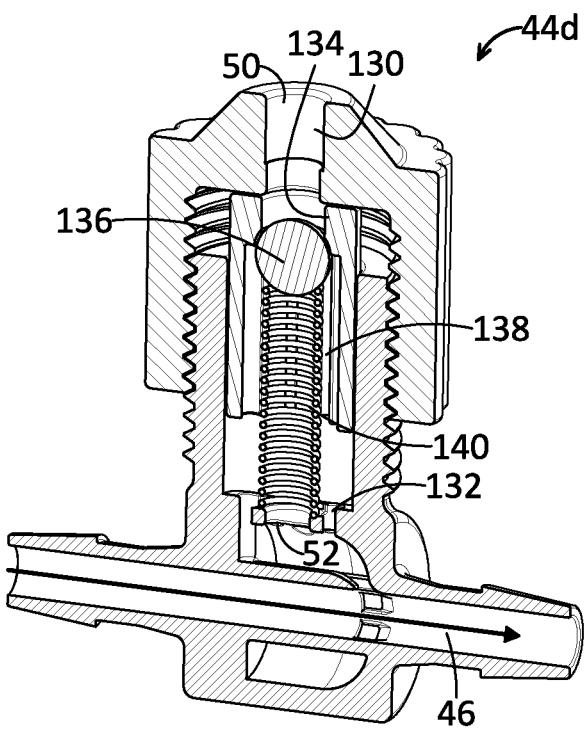
FIG. 11A is a plan view of another embodiment of a passive pressure oscillation assembly used in the aspiration system of FIG. 1, particularly showing the passive pressure oscillation assembly in a closed position.
Figure 11B:
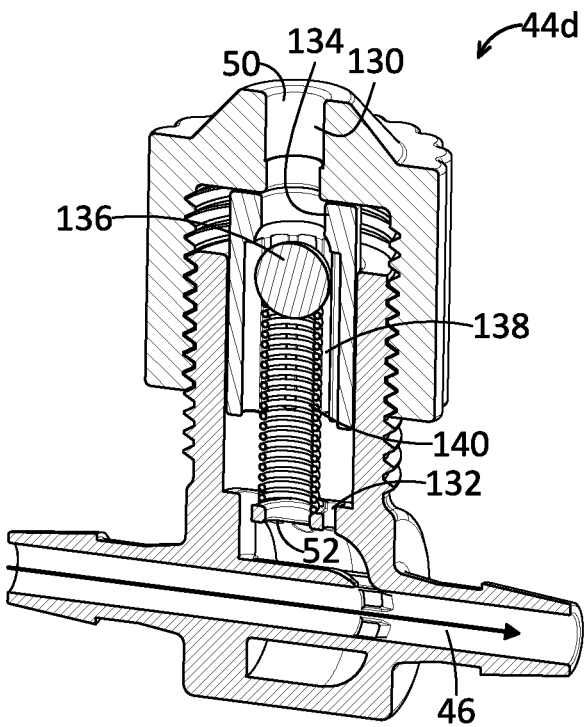
FIG. 11B is a plan view of the passive pressure oscillation assembly of FIG. 11A, particularly showing the passive pressure oscillation assembly in an open position.

It should be noted that the passive pressure oscillation assembly 44*d* illustrated in FIGS. 11A and 11B topologically comprises a pressure actuated valve 54 and a fluid resonator 56 (shown in FIG. 5) that are mechanically coupled to each other. That is, the valve seat 134 and movable valve ball 136 form the pressure actuated valve 54, whereas the valve ball 136, enlarged flow cavity 138, and spring 140 form the fluid resonator 56, with the pressure actuated valve 54 and fluid resonator 56 being mechanically coupled to each other via the valve ball 136. In this embodiment, because the valve ball 136 forms a portion of both the pressure actuated valve 54 and the fluid resonator 56, the negative activation and cessation pressure differentials and the resonance frequency must be designed with due regard to each other, and thus, may not be able to be independently optimized, although the resulting design of the passive pressure oscillation assembly 44*d* may be mechanically simple.

Figure 12:
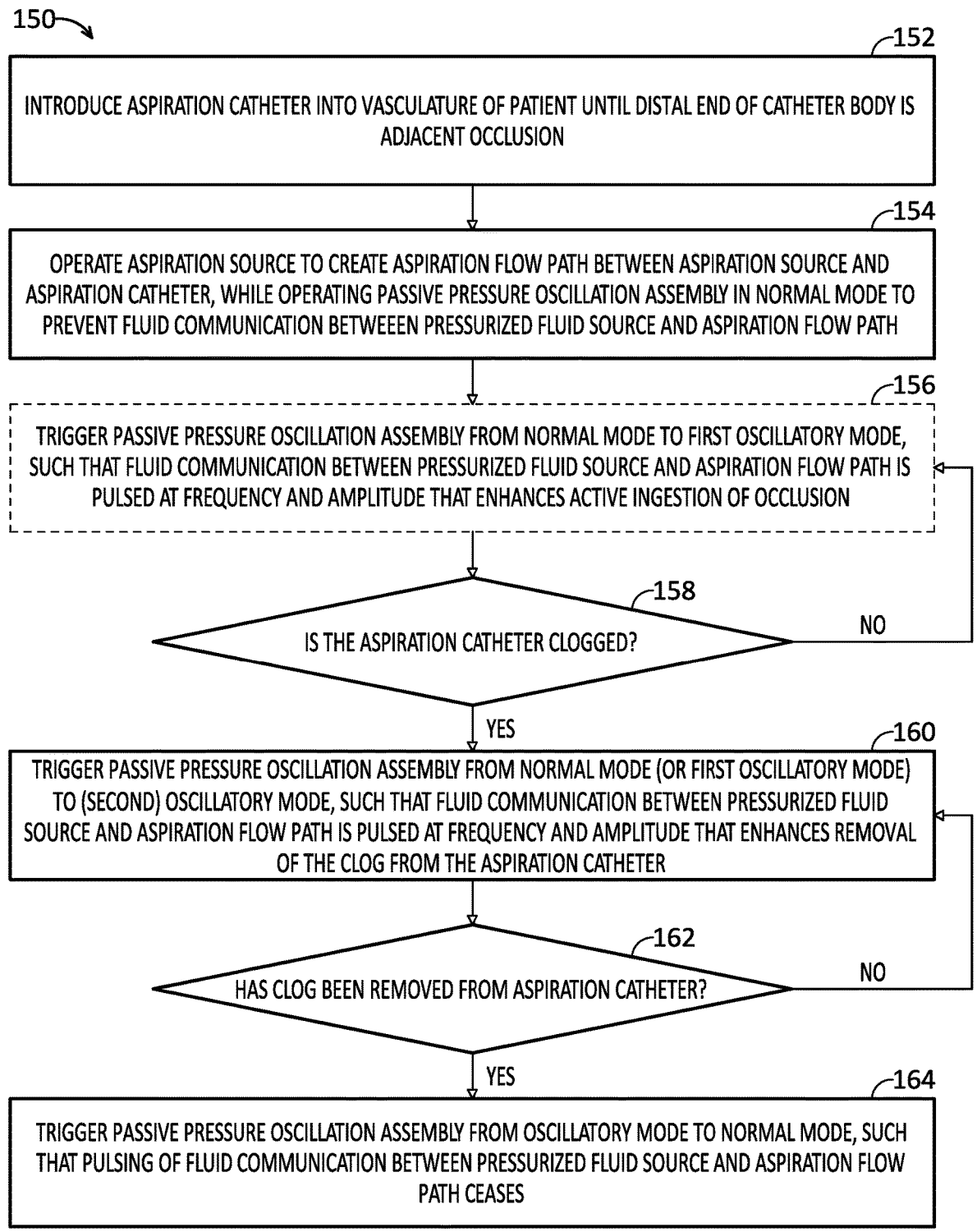
FIG. 12 is a flow diagram illustrating one method of operating the aspiration system of FIG. 1 to aspirate an occlusion from the vasculature of a patient.

Referring now to FIG. 12, one method 150 of operating the aspiration system 10 to aspirate the occlusion 2 from the vasculature 1 of a patient will be described. The method 150 comprises introducing the aspiration catheter 12 into the vasculature 1 of the patient until the distal end 30 of the catheter body 22 is adjacent the occlusion 2 (step 152). Next, the aspiration source 14 is operated to create an aspiration flow path 46 between the aspiration catheter 12 and the aspiration source 14 to actively ingest the occlusion 2, while operating the passive pressure oscillation assembly 44 in the normal mode to prevent fluid communication between the pressurized fluid source 16 and the aspiration flow path 46 (step 154). Thus, aspiration of the occlusion 2 is performed as efficiently as possible at this point.

Optionally, the passive pressure oscillation assembly 44 is triggered to switch from the normal mode to a first oscillatory mode in response to active ingestion of the occlusion 2 (e.g., if the absolute pressure in the aspiration flow path 46 drops to a level that creates a first negative activation pressure differential between the pressurized fluid source 44 and the aspiration flow path 46 less than −50 kPa), such that fluid communication between the pressurized fluid source 16 and the aspiration flow path 46 is pulsed at a suitable amplitude and frequency that enhances active ingestion of the occlusion 2 (e.g., high frequency, low amplitude) (step 156). The high frequency, low amplitude pulsing of the fluid communication between the pressurized fluid source 16 and the aspiration flow path 46 may minimize disruption to the aspiration flow path 46, such that active ingestion of the occlusion 2 may be as efficient as possible.

Next, if a clog occurs in the aspiration conduit 24 of the aspiration catheter 12 (e.g., if the absolute pressure in the aspiration flow path 46 drops to a level that creates a second negative activation pressure differential between the pressurized fluid source 44 and the aspiration flow path 46 less than −55 kPa) (step 158), the passive pressure oscillation assembly 44 is triggered to switch from the normal mode (or optionally the first oscillatory mode) to the (second) oscillatory mode, such that fluid communication between the pressurized fluid source 16 and the aspiration flow path 46 is pulsed at a suitable amplitude and frequency that enhances clearing of the clog (e.g., low frequency, high amplitude) (step 160). Optionally, the fluid communication between the pressurized fluid source 16 and the aspiration flow path 46 may be pulsed simultaneously at different frequencies. If a clog does not occur in the aspiration conduit 24 of the aspiration catheter 12 (e.g., if the absolute pressure in the aspiration flow path 46 does not drop to a level that creates a second negative activation pressure differential between the pressurized fluid source 44 and the aspiration flow path 46 less than −55 kPa) (step 158), the passive pressure oscillation assembly 44 remains in the normal mode (or optionally in the first oscillatory mode) until the occlusion 2 is fully ingested.

If a clog does occur in the aspiration conduit 24 of the aspiration catheter 12, and such clog has been removed, or otherwise the anomaly in the aspiration circuit of the aspiration system 10 has been resolved (e.g., if the absolute pressure in the aspiration flow path 46 rises to a level that creates a negative cessation pressure differential between the pressurized fluid source 44 and the aspiration flow path 46 that is greater, and preferably 10 kPa-25 kPa greater, than the negative activation pressure differential) (step 162), the passive pressure oscillation assembly 44 is triggered to switch from the oscillatory mode to the normal mode, such that fluid communication between the pressurized fluid source 16 and the aspiration flow path 46 is again prevented, and the aspiration procedure continues (step 164). If a clog does occur in the aspiration conduit 24 of the aspiration catheter 12, and such clog has not been removed, or otherwise the anomaly in the aspiration circuit of the aspiration system 10 has not been resolved (e.g., if the absolute pressure in the aspiration flow path 46 does not rise to a level that creates a negative cessation pressure differential between the pressurized fluid source 44 and the aspiration flow path 46 that is greater, and preferably 10 kPa-25 kPa greater, than the negative activation pressure differential), the passive pressure oscillation assembly 44 remains in the (second) oscillator mode until the occlusion 2 has been removed, or otherwise the anomaly in the aspiration circuit of the aspiration system 10 has been resolved.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A method of aspirating an occlusion from a patient, comprising:
   creating an aspiration flow path between an aspiration catheter located adjacent the occlusion and an aspiration source;
   preventing fluid communication between a pressurized fluid source and the aspiration flow path; and
   pressure pulsing fluid between the pressurized fluid source and the aspiration flow path automatically, via a passive pressure oscillation assembly that is without user input and without an electronic sensor, in response to a clog in the aspiration catheter.

2. The method of claim 1, wherein pressure pulsing fluid between the pressurized fluid source and the aspiration flow path causes pressure pulses to propagate in the aspiration flow path.

3. The method of claim 1, wherein pressure pulsing fluid between the pressurized fluid source and the aspiration flow path causes fluid backflows to propagate in the aspiration flow path.

4. The method of claim 1, wherein the pressurized fluid source comprises one of ambient air and a reservoir containing a liquid.

5. The method of claim 1, further comprising ceasing pressure pulsing of the fluid between the pressurized fluid source and the aspiration flow path automatically in response to removal of the clog in the aspiration catheter.

6. The method of claim 1, wherein fluid between the pressurized fluid source and the aspiration flow path is simultaneously pulsed at two different frequencies.

7. The method of claim 1, wherein pressure pulsing fluid between the pressurized fluid source and the aspiration flow path automatically in response to a clog in the aspiration catheter comprises interrupting the aspiration flow path, such that the pulsing fluid between the pressurized fluid source and the aspiration flow path is directed towards the aspiration catheter.

8. The method of claim 1, wherein pressure pulsing fluid between the pressurized fluid source and the aspiration flow path is automatically pulsed in accordance with an oscillatory mode that is triggered in response to the clog in the aspiration catheter.

9. The method of claim 1, wherein the occlusion is a thrombus located in a blood vessel of the patient.

10. The method of claim 1, wherein a manifold is in fluid communication between the pressurized fluid source and the aspiration flow path and comprises the passive pressure oscillation assembly.

11. A method of aspirating an occlusion from a patient, comprising:
    creating an aspiration flow path between an aspiration catheter located adjacent the occlusion and an aspiration source;
    preventing fluid communication between a pressurized fluid source and the aspiration flow path; and
    pressure pulsing fluid between the pressurized fluid source and the aspiration flow path automatically, via a passive pressure oscillation assembly that is without user input and without an electronic sensor, in response to a drop in absolute pressure in the aspiration flow path that creates a negative activation pressure differential between the pressurized fluid source and the aspiration flow path equal to or less than −55 kPa.

12. The method of claim 11, wherein pressure pulsing fluid between the pressurized fluid source and the aspiration flow path causes pressure pulses to propagate in the aspiration flow path.

13. The method of claim 11, wherein pressure pulsing fluid between the pressurized fluid source and the aspiration flow path causes fluid backflows to propagate in the aspiration flow path.

14. The method of claim 11, wherein the pressurized fluid source comprises one of ambient air and a reservoir containing a liquid.

15. The method of claim 11, wherein the negative activation pressure differential is in the range of −55 kPa to −95 kPa.

16. The method of claim 11, further comprising ceasing pressure pulsing fluid between the pressurized fluid source and the aspiration flow path automatically in response to a rise in absolute pressure in the aspiration flow path that creates a negative cessation pressure differential between the pressurized fluid source and the aspiration flow path greater than the negative activation pressure differential.

17. The method of claim 16, wherein the negative cessation pressure differential is 10 kPa-25 kPa greater than the negative activation pressure differential.

18. The method of claim 11, wherein pressure pulsing fluid between the pressurized fluid source and the aspiration flow path is simultaneously pulsed at two different frequencies.

19. The method of claim 11, wherein fluid between the pressurized fluid source and the aspiration flow path is automatically pressure pulsed in accordance with an oscillatory mode of the passive pressure oscillation assembly that is triggered in response to the drop in absolute pressure in the aspiration flow path that creates the negative activation pressure differential between the pressurized fluid source and the aspiration flow path equal to or less than −55 kPa.

20. The method of claim 19, wherein the occlusion is a thrombus located in a blood vessel of the patient.

21. The method of claim 11, wherein a manifold is in fluid communication between the pressurized fluid source and the aspiration flow path and comprises the passive pressure oscillation assembly.

* * * * *